United States Patent
Smith et al.

(10) Patent No.: US 10,296,715 B1
(45) Date of Patent: May 21, 2019

(54) ELECTRONIC PRIOR AUTHORIZATION SYSTEMS AND METHODOLOGIES

(71) Applicant: ALLSCRIPTS SOFTWARE, LLC, Chicago, IL (US)

(72) Inventors: Stephen E. Smith, Richmond, VA (US); Stanislav Makarskyy, Buffalo Grove, IL (US)

(73) Assignee: Allscripts Software, LLC, Chicago, IL (US)

( * ) Notice: Subject to any disclaimer, the term of this patent is extended or adjusted under 35 U.S.C. 154(b) by 824 days.

(21) Appl. No.: 14/320,355

(22) Filed: Jun. 30, 2014

Related U.S. Application Data

(63) Continuation of application No. 14/144,629, filed on Dec. 31, 2013, now abandoned.

(51) Int. Cl.
*G06Q 40/00* (2012.01)
*G06F 19/00* (2018.01)
*G16H 10/60* (2018.01)

(52) U.S. Cl.
CPC ........... *G06F 19/328* (2013.01); *G16H 10/60* (2018.01)

(58) Field of Classification Search
CPC .............................. G16H 10/60; G06F 19/328
USPC ......................................................... 705/2–4
See application file for complete search history.

(56) References Cited

U.S. PATENT DOCUMENTS

| | | | |
|---|---|---|---|
| 8,265,959 B2 * | 9/2012 | McKenzie et al. | 705/3 |
| 8,392,214 B1 * | 3/2013 | Pinsonneault | 705/2 |
| 2006/0116907 A1 * | 6/2006 | Rhodes et al. | 705/2 |
| 2011/0295618 A1 * | 12/2011 | Naipaul et al. | 705/3 |

* cited by examiner

*Primary Examiner* — Mark Holcomb
(74) *Attorney, Agent, or Firm* — Medley, Behrens & Lewis, LLC

(57) ABSTRACT

A method includes accessing from a predictive data mart at a cloud platform which contains historical data on prior authorization transactions, historical transaction data corresponding to information indicated to be necessary for authorization decisions by a payer for use of a proposed medication for treatment of a condition. The method further includes determining, based on the accessed historical transaction data, a most probable question set necessary for an authorization decision by the payer for use of the proposed medication for treatment of the condition.

20 Claims, 27 Drawing Sheets

| PAInitiationRequest | |
|---|---|
| | requestID |
| | patientData |
| | conditionData |
| | medicationData |

FIG. 2

PAInitiationRequest requestID
planData
conditionData
medicationData

FIG. 3

| PAInitiationRequest |
|---|
| requestID |
| patientData |
| planData |
| conditionData |
| medicationData |

*FIG. 4*

PAInitiationResponse
- requestID
- authNeeded
- questionSet
  - question1
  - question2
  - ...
  - questionN

FIG. 6B user1 ▷

Smith, Sally A.
Age: 31 | Sex F | MRN 933145526

Condition: Attention Deficit Hyperactivity Disorder

Insurer: Acme Health Insurance

Proposed Medication: Ritalin

Prior Approval Required: Acme Health Insurance has authorized 14% of Ritalin requests for patients with these conditions. 3% of appeals for denial of this medication have been approved.

Alternative Medication: Adderall

Prior Approval Required: Acme Health Insurance has authorized 64% of Adderall requests for patients with these conditions. 15% of appeals for denial of this medication have been approved.

*FIG. 15*

ELECTRONIC PRIOR AUTHORIZATION SYSTEMS AND METHODOLOGIES

CROSS-REFERENCE TO RELATED APPLICATION

The present application is a U.S. continuation patent application of, and claims priority under 35 U.S.C. § 120 to, U.S. nonprovisional patent application Ser. No. 14/144,629, filed Dec. 31, 2013, which patent application and any patent application publications thereof and patents issuing therefrom are hereby incorporated herein by reference. The present application further hereby incorporates herein by reference the entire disclosure of Appendix A attached hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to insurance authorization.

Frequently, a healthcare insurance provider will require authorization prior to care provision or subscription. For example, insurance providers commonly require prior authorization (PA) based on a patient's insurance plan, medical condition, and the medication or treatment being prescribed. This has traditionally been a manual process, but in January 2013, the National Council for Prescription Drug Programs, (NCPDP) an ANSI-accredited, standards development organization providing healthcare solutions, announced extensions to their messaging standard to include prior authorization.

Needs exist for improvement in electronic authorization. These, and other needs, are addressed by one or more aspects of the present invention.

SUMMARY OF THE INVENTION

The present invention includes many aspects and features. Moreover, while many aspects and features relate to, and are described in, the context of health care, the present invention is not limited to use only in this context, as will become apparent from the following summaries and detailed descriptions of aspects, features, and one or more embodiments of the present invention.

Accordingly, one aspect of the present invention relates to a method which includes receiving, at a cloud platform from an electronic health records application, an initiation request including an identifier associated with a patient, an indication of a condition of the patient, and an indication of a proposed medication. The initiation request is forwarded to a payer, and a copy stored at the cloud platform. An initiation response from the payer which includes a question set is received at the cloud platform. One or more questions from the question set are presented via the electronic health records application, and answers provided by a care giver. Data corresponding to the answers is communicated in an authorization request to the payer. A copy of the authorization request is stored at the cloud platform. The payer returns an authorization response, either authorizing or denying use of the proposed medication. The cloud platform stores data related to the transactions in a predictive data mart.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a transaction hub of a cloud platform, an initiation request including an identifier associated with the patient, an indication of the condition of the patient, and an indication of the proposed medication; storing, at a message store of the cloud platform, data corresponding to the initiation request; effecting forwarding, by the transaction hub, of the initiation request to a payer platform; receiving from the payer platform, at the transaction hub of the cloud platform, an initiation response including a question set corresponding to information that is needed by the payer for authorization of the medication for treatment of the condition for the patient; storing, at the message store of the cloud platform, data corresponding to the initiation response; communicating, by the cloud platform, data associated with the question set to the electronic health records application; displaying, via a display screen associated the electronic device, a question to the care giver based on the data associated with the question set communicated to the electronic health records application; receiving, from the caregiver via one or more input devices associated with the electronic device, second user input corresponding to an answer to the displayed question; communicating, from the electronic health records application to the cloud platform, data associated with the answer to the displayed question; communicating, from the cloud platform to the payer platform, an authorization request including data associated with the answer to the displayed question; storing, at the message store of the cloud platform, data corresponding to the authorization request; receiving, at the cloud platform from the payer platform, an authorization response including an indication of whether authorization of the medication for treatment of the condition for the patient is granted; storing, at the message store of the cloud platform, data corresponding to the authorization response; and performing, at the cloud platform, analytics processing by aggregating data, including the data corresponding to the initialization request, initialization response, authorization request, and storing the aggregated data in a predictive data mart.

In a feature of this aspect, the electronic device comprises a tablet.

In a feature of this aspect, the electronic device comprises a laptop.

In a feature of this aspect, the electronic device comprises a phone.

In a feature of this aspect, receiving first user input comprises receiving first user input input via a touchscreen.

In a feature of this aspect, receiving first user input comprises receiving first user input input via a mouse and keyboard.

In a feature of this aspect, the identifier comprises a patient identifier.

In a feature of this aspect, the identifier comprises a plan identifier.

In a feature of this aspect, the identifier comprises a social security number.

In a feature of this aspect, the indication of the condition of the patient comprises a medical code.

In a feature of this aspect, the indication of the medication comprises an identification number associated with a medication.

In a feature of this aspect, the identifier comprises a patient identification number.

In a feature of this aspect, the electronic health records application is loaded on the electronic device.

In a feature of this aspect, the electronic health records application is a cloud based electronic health records application.

Another aspect relates to a method comprising receiving, at an electronic health records application loaded on an electronic device, first user input from a care giver input via one or more input devices associated with an electronic device, the first user input corresponding to an indication of a proposed medication for treatment of a condition of a patient; communicating, from the electronic health records application to a cloud platform, an initiation request including an identifier associated with the patient, an indication of the condition of the patient, and an indication of the proposed medication; storing, at the cloud platform, data corresponding to the initiation request; effecting forwarding, by the cloud platform, of the initiation request to a payer platform; receiving from the payer platform, at the cloud platform, an initiation response including a question set corresponding to information that is needed by the payer for authorization of the medication for treatment of the condition for the patient; storing, at the cloud platform, data corresponding to the initiation response; communicating, by the cloud platform, data associated with the question set to the electronic health records application; displaying, via a display screen associated the electronic device, a question to the care giver based on the data associated with the question set communicated to the electronic health records application; receiving, from the caregiver via one or more input devices associated with the electronic device, second user input corresponding to an answer to the displayed question; communicating, from the electronic health records application to the cloud platform, data associated with the answer to the displayed question; communicating, from the cloud platform to the payer platform, an authorization request including data associated with the answer to the displayed question; storing, at the cloud platform, data corresponding to the authorization request; receiving, at the cloud platform from the payer platform, an authorization response including an indication of whether authorization of the medication for treatment of the condition for the patient is granted; storing, at the cloud platform, data corresponding to the authorization response; and performing, at the cloud platform, analytics processing by aggregating data, including the data corresponding to the initialization request, initialization response, authorization request, and storing the aggregated data in a predictive data mart.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a transaction hub of a cloud platform, an initiation request including an identifier associated with the patient, an indication of the condition of the patient, and an indication of the proposed medication; storing, at a message store of the cloud platform, data corresponding to the initiation request; effecting forwarding, by the transaction hub, of the initiation request to a payer platform; receiving from the payer platform, at the transaction hub of the cloud platform, an initiation response including a question set corresponding to information that is needed by the payer for authorization of the medication for treatment of the condition for the patient; storing, at the message store of the cloud platform, data corresponding to the initiation response; communicating, by the cloud platform, data associated with the question set to the electronic health records application; displaying, via a display screen associated the electronic device, a question to the care giver based on the data associated with the question set communicated to the electronic health records application; receiving, from the caregiver via one or more input devices associated with the electronic device, second user input corresponding to an answer to the displayed question; communicating, from the electronic health records application to the cloud platform, data associated with the answer to the displayed question; communicating, from the cloud platform to the payer platform, an authorization request including data associated with the answer to the displayed question; storing, at the message store of the cloud platform, data corresponding to the authorization request; receiving, at the cloud platform from the payer platform, an authorization response including an indication of whether authorization of the medication for treatment of the condition for the patient is granted; storing, at the message store of the cloud platform, data corresponding to the authorization response; and performing, at the cloud platform, analytics processing by aggregating data, including the data corresponding to the initialization request, initialization response, authorization request, and storing the aggregated data in a predictive data mart.

In a feature of this aspect, the electronic device comprises a computer.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from a predictor module associated with the electronic health records application to a predictor service at a cloud platform, data corresponding to an identification of a payer associated with the patient, an identification of the condition, and an identification of the proposed medication; accessing, by the predictor service at the cloud platform from a predictive data mart at the cloud platform which contains historical data on prior authorization transactions, historical transaction data corresponding to historical authorization decisions by the payer for use of the proposed medication for treatment of the condition, and historical authorization decisions by the payer for use of one or more other medications for treatment of the condition; determining, by the predictor service based on the accessed historical transaction data, a probability value that an authorization request for use of the proposed medication for treatment of the condition will be approved by the payer; determining, by the predictor service based on the accessed historical transaction data, a probability value that an authorization request for use of the each of the one or more other medications for treatment of the condition will be approved by the payer; communicating data corresponding to the determined probability values to the predictor module; and displaying, to the care giver via a user interface displayed on a display screen associated with the electronic device, an indication of the proposed medication together with the corresponding determined probability value, and an indication of each of the one or more other medications for treatment of the condition together with a corresponding determined probability value for each.

In a feature of this aspect, the electronic device comprises a tablet.

In a feature of this aspect, the electronic device comprises a laptop.

In a feature of this aspect, the electronic device comprises a phone.

In a feature of this aspect, receiving first user input comprises receiving first user input input via a touchscreen.

In a feature of this aspect, receiving first user input comprises receiving first user input input via a mouse.

In a feature of this aspect, receiving first user input comprises receiving first user input input via a keyboard.

In a feature of this aspect, the identification of the condition of the patient comprises a medical code.

In a feature of this aspect, the identification of the medication comprises an identification number associated with a medication.

In a feature of this aspect, the identification of the payer comprises a payer code.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from a predictor module associated with the electronic health records application to a predictor service at a cloud platform, data corresponding to an identification of a payer associated with the patient, an identification of the condition, and an identification of the proposed medication; accessing, by the predictor service at the cloud platform from a predictive data mart at the cloud platform which contains historical data on prior authorization transactions, historical transaction data corresponding to historical authorization decisions by the payer for use of the proposed medication for treatment of the condition; determining, by the predictor service based on the accessed historical transaction data, a probability value that an authorization request for use of the proposed medication for treatment of the condition will be approved by the payer; communicating data corresponding to the determined probability value to the predictor module; and displaying, to the care giver via a user interface displayed on a display screen associated with the electronic device, the determined probability value.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a cloud platform, data corresponding to an identification of a payer associated with the patient, an identification of the condition, and an identification of the proposed medication; accessing, at the cloud platform from a predictive data mart at the cloud platform which contains historical data on prior authorization transactions, historical transaction data corresponding to historical authorization decisions by the payer for use of the proposed medication for treatment of the condition; determining, by the predictor service based on the accessed historical transaction data, a probability value that an authorization request for use of the proposed medication for treatment of the condition will be approved by the payer; communicating data corresponding to the determined probability value to the predictor module; and displaying, to the care giver via a user interface displayed on a display screen associated with the electronic device, the determined probability value.

Another aspect relates to a method which includes communicating, from an electronic health records application to a cloud platform, data corresponding to an identification of a payer associated with a patient, an identification of a condition, and an identification of a proposed medication; accessing, at the cloud platform from a predictive data mart, historical transaction data corresponding to historical authorization decisions by the payer for use of the proposed medication for treatment of the condition; determining, by the predictor service based on the accessed historical transaction data, a probability value that an authorization request for use of the proposed medication for treatment of the condition will be approved by the payer; communicating data corresponding to the determined probability value to the predictor module; and displaying, to the care giver via a user interface displayed on a display screen associated with the electronic device, the determined probability value.

Another aspect relates to a method which includes receiving, at an electronic health records application, first user input from a care giver input via one or more input devices associated with an electronic device, the first user input corresponding to an indication of a proposed medication for treatment of a condition of a patient; communicating, from the electronic health records application to a predictor service at a cloud platform, data corresponding to an identification of a payer associated with the patient, an identification of the condition, and an identification of the proposed medication; accessing, by the predictor service at the cloud platform from a predictive data mart at the cloud platform which contains historical data on prior authorization transactions, historical transaction data corresponding to information indicated to be necessary for authorization decisions by the payer for use of the proposed medication for treatment of the condition; determining, by the predictor service based on the accessed historical transaction data, a most probable question set necessary for an authorization decision by the payer for use of the proposed medication for treatment of the condition; communicating, by the cloud platform, data associated with the most probable question set to the electronic health records application; displaying, via a display screen associated with the electronic device, a question to the care giver based on the data associated with the most probable question set communicated to the electronic health records application; receiving, from the caregiver via one or more input devices associated with the electronic device, second user input corresponding to an answer to the displayed question; communicating, from the electronic health records application to the cloud platform, data associated with the answer to the displayed question; communicating, from the cloud platform to a platform associated with the payer, an authorization request including data associated with the answer to the displayed question; and receiving, at the cloud platform from the platform associated with the payer, an authorization response including an indication of whether authorization of the medication for treatment of the condition for the patient is granted, and communicating data corresponding to such indication to the electronic health records application.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a predictor service at a cloud platform, data corresponding to an identification of a payer associated with the patient, an identification of the condition, and an identification of the proposed medication; accessing, by the predictor service at the cloud platform from a predictive data mart at the cloud platform which contains historical data on prior authorization transactions, historical transaction data corresponding to question sets for authorization decisions by the payer for use of the proposed medication for treatment of the condition; determining, by the predictor service based on the accessed historical transaction data, a most probable question set necessary for an authorization decision by the payer for use of the proposed medication for treatment of the condition; communicating, by the cloud platform, data associated with the most probable question set to the electronic health records application; displaying, via a display screen associated with the electronic device, a question to the care giver based on the data associated with the most probable question set communicated to the electronic health records application; receiving, from the caregiver via one or more input devices associated with the electronic device, second user input corresponding to an answer to the displayed question; communicating, from the electronic health records application to the cloud platform, data associated with the answer to the displayed question; communicating, from the cloud platform to a platform associated with the payer, an authorization request including data associated with the answer to the displayed question; and receiving, at the cloud platform from the platform associated with the payer, an authorization response including an indication of whether authorization of the medication for treatment of the condition for the patient is granted, and communicating data corresponding to such indication to the electronic health records application.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a cloud platform, data corresponding to an identification of a payer associated with the patient, an identification of the condition, and an identification of the proposed medication; accessing, by the cloud platform from a predictive data mart at the cloud platform which contains historical data on prior authorization transactions, historical transaction data corresponding to information indicated to be necessary for authorization decisions by the payer for use of the proposed medication for treatment of the condition; determining, based on the accessed historical transaction data, a most probable question set necessary for an authorization decision by the payer for use of the proposed medication for treatment of the condition; displaying, via a display screen associated with the electronic device, a question to the care giver based on the determined most probable question; receiving, from the caregiver via one or more input devices associated with the electronic device, second user input corresponding to an answer to the displayed question; communicating, from the cloud platform to a platform associated with the payer, an authorization request including data associated with the answer to the displayed question; and receiving, at the cloud platform from the platform associated with the payer, an authorization response including an indication of whether authorization of the medication for treatment of the condition for the patient is granted, and communicating data corresponding to such indication to the electronic health records application.

Another aspect relates to a method comprising receiving, at an electronic health records application, first user input from a care giver input via one or more input devices associated with an electronic device, the first user input corresponding to an indication of a proposed medication for treatment of a condition of a patient; communicating, from the electronic health records application to a cloud platform, an initiation request including an identifier associated with the patient, an indication of the condition of the patient, and an indication of the proposed medication; effecting forwarding, by the cloud platform, of the initiation request to a payer platform; receiving from the payer platform, at the cloud platform, an initiation response including a question set corresponding to information that is needed by the payer for authorization of the medication for treatment of the condition for the patient; communicating, by the cloud platform, the question set to a question set helper module; parsing, by the question set helper module, the question set, determining a first question for presentation, and communicating data associated with the determined first question to the electronic health records application; displaying, by the electronic health records application based on the received data associated with the determined first question, a user interface including the first question to the care giver; receiving, from the care giver via one or more input devices associated with the electronic device, second user input corresponding to an answer to the displayed first question; communicating, from the electronic health records application to the question set helper module, data associated with the answer to the displayed first question; determining, at the question set helper module based on the communicated data associated with the answer to the displayed first question, a second question for presentation, and communicating data associated with the determined second question to the electronic health records application; displaying, by the electronic health records application based on the received data associated with the determined second question, a user interface including the second question to the care giver; receiving, from the care giver via one or more input devices associated with the electronic device, third user input corresponding to an answer to the displayed second question; communicating, from the electronic health records application to the question set helper module, data associated with the answer to the displayed second question; effecting communication to the payer platform, based on the answers to the displayed first and second questions, of an authorization request including data associated with the answers to the first and second questions; and receiving, at the cloud platform from the payer platform, an authorization response including an indication of whether authorization of the medication for treatment of the condition for the patient is granted.

Another aspect relates to a method comprising receiving, at an electronic health records application, first user input from a care giver input via one or more input devices associated with an electronic device, the first user input corresponding to an indication of a proposed medication for treatment of a condition of a patient; effecting communication, from the electronic health records application to a payer platform, of an initiation request including an identifier associated with the patient, an indication of the condition of the patient, and an indication of the proposed medication; receiving, at the electronic health records application, an initiation response including a question set corresponding to information that is needed by the payer for authorization of the medication for treatment of the condition for the patient; communicating, by the electronic health records application, the question set to a question set helper module; parsing, by the question set helper module, the question set, determining a first question for presentation, and communicating data associated with the determined first question to the electronic health records application; displaying, by the electronic health records application based on the received data associated with the determined first question, a user interface including the first question to the care giver; receiving, from the care giver via one or more input devices associated with the electronic device, second user input corresponding to an answer to the displayed first question; communicating, from the electronic health records application to the question set helper module, data associated with the answer to the displayed first question; determining, at the question set helper module based on the communicated data associated with the answer to the displayed first question, a second question for presentation, and communicating data associated with the determined second question to the electronic health records application; displaying, by the electronic health records application based on the received data associated with the determined second question, a user interface including the second question to the care giver; receiving, from the care giver via one or more input devices associated with the electronic device, third user input corresponding to an answer to the displayed second question; communicating, from the electronic health records application to the question set helper module, data associated with the answer to the displayed second question; effecting communication to the payer platform, based on the answers to the displayed first and second questions, of an authorization request including data associated with the answers to the first and second questions; and receiving, at the electronic health records application, an authorization response including an indication of whether authorization of the medication for treatment of the condition for the patient is granted.

Another aspect relates to a method which includes receiving, at an electronic health records application, first user input from a care giver input via one or more input devices associated with an electronic device, the first user input corresponding to an indication of a proposed medication for treatment of a condition of a patient; communicating, from the electronic health records application to a predictor service at a cloud platform, data corresponding to an identification of a payer associated with the patient, an identification of the condition, and an identification of the proposed medication; accessing, by the predictor service at the cloud platform from a predictive data mart at the cloud platform which contains historical data on prior authorization transactions, historical transaction data corresponding to information indicated to be necessary for authorization decisions by the payer for use of the proposed medication for treatment of the condition; determining, by the predictor service based on the accessed historical transaction data, a most probable question set necessary for an authorization decision by the payer for use of the proposed medication for treatment of the condition; communicating, by the cloud platform, data associated with the most probable question set to the electronic health records application; communicating, by the electronic health records application, the question set to a question set helper module; parsing, by the question set helper module, the question set, determining a first question for presentation, and communicating data associated with the determined first question to the electronic health records application; displaying, by the electronic health records application based on the received data associated with the determined first question, a user interface including the first question to the care giver; receiving, from the care giver via one or more input devices associated with the electronic device, second user input corresponding to an answer to the displayed first question; communicating, from the electronic health records application to the question set helper module, data associated with the answer to the displayed first question; determining, at the question set helper module based on the communicated data associated with the answer to the displayed first question, a second question for presentation, and communicating data associated with the determined second question to the electronic health records application; displaying, by the electronic health records application based on the received data associated with the determined second question, a user interface including the second question to the care giver; receiving, from the care giver via one or more input devices associated with the electronic device, third user input corresponding to an answer to the displayed second question; communicating, from the electronic health records application to the question set helper module, data associated with the answer to the displayed second question; effecting communication to the payer platform, based on the answers to the displayed first and second questions, of an authorization request including data associated with the answers to the first and second questions; and receiving, at the electronic health records application, an authorization response including an indication of whether authorization of the medication for treatment of the condition for the patient is granted.

Another aspect relates to a method which includes displaying one or more user interfaces associated with a question set manager of a cloud platform, receiving user input from a pharmacy benefits manager (PBM) user corresponding to an indication of first and second questions to be included in a question set and conditional logic linking the first and second questions. The method further includes hosting, in the cloud platform at the question set manager, a question set developed using the question set manager, the question set including the first and second questions and the conditional logic linking the first and second questions. The method further includes subsequently retrieving the hosted question from the cloud platform via a question set service in response to a prior authorization initiation request received at a system associated with the PBM, and including the retrieved question set in a prior authorization initiation response.

Another aspect relates to a method comprising displaying, via a display of a first electronic device, one or more user interfaces associated with a question set manager of a cloud platform configured to allow a user to configure a question set; receiving first user input from a pharmacy benefits manager (PBM) user input via one or more input devices associated with the first electronic device, the first user input corresponding to an indication of a first question to be included in a question set; receiving second user input from the PBM user input via one or more input devices associated with the first electronic device, the second user input corresponding to an indication of a second question to be included in a question set; receiving third user input from the PBM user input via one or more input devices associated with the electronic device, the third user input corresponding to an indication of conditional logic linking the first and second questions; hosting, in the cloud platform at the question set manager, a question set developed using the question set manager, the question set including the first and second questions and the conditional logic linking the first and second questions; receiving, at a PBM system comprising one or more electronic devices associated with the PBM, a prior authorization initiation request including an identifier associated with a patient, an indication of a condition of a patient, and an indication of a proposed medication; invoking, by the PBM system, a question set service of the cloud platform; retrieving, by the question set service of the cloud platform from the question set manager of the cloud platform, the hosted question set; communicating, from the question set service of the cloud platform to the PBM system, the hosted question set; and communicating, by the PBM system in response to the received prior authorization initiation request, a prior authorization initiation response including the received question set.

In a feature of this aspect, the first electronic device comprises a tablet.

In a feature of this aspect, the first electronic device comprises a laptop.

In a feature of this aspect, the first electronic device comprises a phone.

In a feature of this aspect, the first electronic device comprises a computer.

In a feature of this aspect, receiving first user input comprises receiving first user input input via a touchscreen.

In a feature of this aspect, receiving first user input comprises receiving first user input input via a mouse.

In a feature of this aspect, receiving first user input comprises receiving first user input input via a keyboard.

In a feature of this aspect, the PBM system comprises one or more servers.

In a feature of this aspect, the PBM system comprises a personal computer.

Another aspect relates to a method comprising displaying, via a display of a first electronic device, one or more user interfaces associated with a question set manager of a cloud platform configured to allow a user to configure a question set; receiving first user input from a payer user input via one or more input devices associated with the first electronic device, the first user input corresponding to an indication of a first question to be included in a question set; receiving second user input from the payer user input via one or more input devices associated with the first electronic device, the second user input corresponding to an indication of a second question to be included in a question set; receiving third user input from the payer user input via one or more input devices associated with the electronic device, the third user input corresponding to an indication of conditional logic linking the first and second questions; hosting, in the cloud platform at the question set manager, a question set developed using the question set manager, the question set including the first and second questions and the conditional logic linking the first and second questions; receiving, at a payer platform comprising one or more electronic devices associated with the payer, a prior authorization initiation request including an identifier associated with a patient, an indication of a condition of a patient, and an indication of a proposed medication; invoking, by the payer platform, a question set service of the cloud platform; retrieving, by the question set service of the cloud platform from the question set manager of the cloud platform, the hosted question set; communicating, from the question set service of the cloud platform to the payer platform, the hosted question set; and communicating, by the payer platform in response to the received prior authorization initiation request, a prior authorization initiation response including the received question set.

In a feature of this aspect, the payer platform comprises one or more servers.

Another aspect relates to a method which includes displaying, via a display of a first electronic device, one or more user interfaces associated with a question set manager of a cloud platform configured to allow a user to configure a question set; receiving first user input from a pharmacy benefits manager (PBM) user input via one or more input devices associated with the first electronic device, the first user input corresponding to an indication of a first question to be included in a question set; receiving second user input from the PBM user input via one or more input devices associated with the first electronic device, the second user input corresponding to an indication of a second question to be included in a question set; receiving third user input from the PBM user input via one or more input devices associated with the electronic device, the third user input corresponding to an indication of conditional logic linking the first and second questions; and hosting, in the cloud platform at the question set manager, a question set developed using the question set manager, the question set including the first and second questions and the conditional logic linking the first and second questions.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIGS. 2-4 illustrate from a high level perspective exemplary prior authorization initiation requests that might be utilized in one or more preferred implementations;

FIG. 6B illustrates from a high level perspective an exemplary prior authorization initiation response that includes a question set that might be utilized in one or more preferred implementations when it has been determined that prior authorization is required;

FIG. 15 illustrates an exemplary user interface for an EHR application;

DETAILED DESCRIPTION

Figure 1:
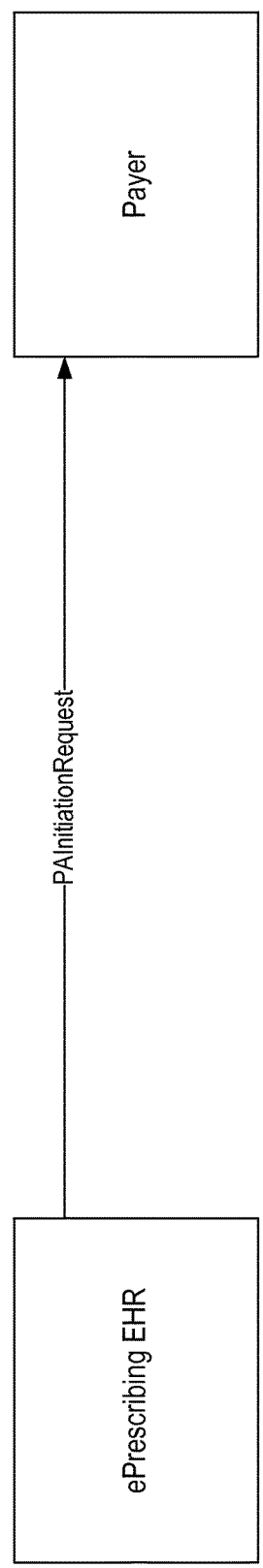
FIG. 1 illustrates communication of a prior authorization initiation request in accordance with one or more preferred implementations.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Electronic Prior Authorization (ePA) is a set of NCPDP transactions that form a workflow between a healthcare platform for a care giver and an associated platform of one or more external payers (e.g., insurance companies). In this workflow, an ePrescribing product inquires of a payer if prior authorization is required for a medication or treatment, based on a patient's medical condition and insurance plan. If prior authorization is required, the payer returns a question set to which the care giver's system must respond. Based on the care giver's answers, the payer either authorizes or denies the ePA request.

In one or more preferred implementations, this process begins with a prior authorization initiation request (PAInitiationRequest), as illustrated in FIG. 1. In one or more preferred implementations, a PAInitiationRequest includes data associated with a patient or plan, data associated with a medical condition, and data associated with a medication or other treatment. For example, a request might be sent for John Doe for treatment of the medical condition Attention Deficit Hyperactivity Disorder (ADHD) with Adderall. This request might include one or more identifiers associated with John Doe (such as a patient ID, subscriber ID, or Social Security Number), or information corresponding to an insurance plan (such as a plan number) of John Doe, or both. FIGS. 2-4 illustrate from a high level perspective exemplary PAInitiationRequests that might be utilized in one or more preferred implementations.

In one or more preferred implementations, once such a PAInitiationRequest from a ePrescribing EHR is received at a payer platform, the payer platform determines, based on the information in the PAInitiationRequest, whether prior authorization is required for use of the specified treatment or medication by the specified patient (and/or under the specified plan) for the specified condition.

Preferably, if it is determined that prior authorization is not necessary, a PAInitiationResponse is sent to the ePrescribing EHR which contains an indication that prior authorization is not necessary. If, on the other hand, it is determined that prior authorization is required, then a question set is provided in the PAInitiationResponse which indicates information or answers that the payer will need to make a determination as to whether to authorize treatment (that is, provide prior authorization).

Figure 5:
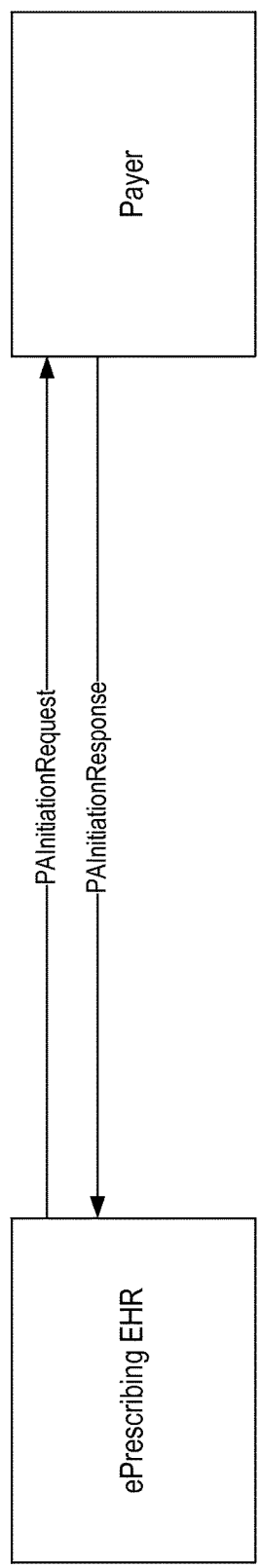
FIG. 5 illustrates communication of a prior authorization initiation response by a payer platform which received a prior authorization initiation request from an ePrescribing HER.
Figure 6A:
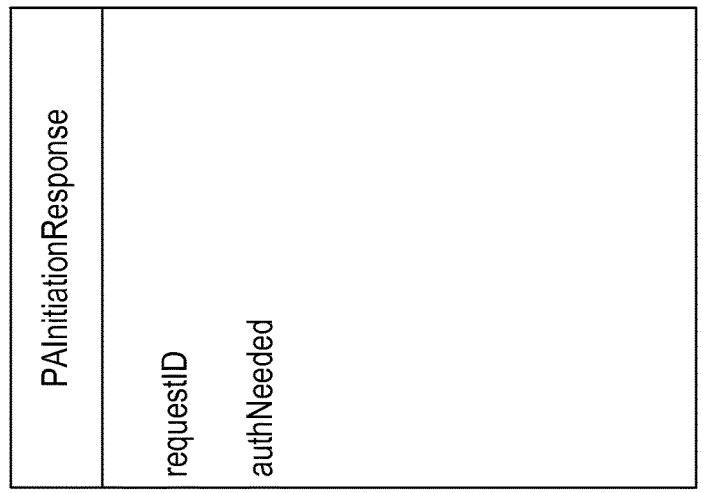
FIG. 6A illustrates from a high level perspective an exemplary prior authorization initiation response that might be utilized in one or more preferred implementations when it has been determined that prior authorization is not required.

FIG. 5 illustrates communication of a PAInitiationResponse by a payer platform which received a PAInitiation Request from an ePrescribing EHR. FIG. 6A illustrates from a high level perspective an exemplary PAInitiationResponse that might be utilized in one or more preferred implementations when it has been determined that prior authorization is not required, while FIG. 6B illustrates from a high level perspective an exemplary PAInitiationResponse that includes a question set that might be utilized in one or more preferred implementations when it has been determined that prior authorization is required.

As illustrated, a PAInitiationResponse preferably includes an identifier associated with the request in order to allow it to be easily discerned what request a particular message corresponds to.

Preferably, following receipt of a PAInitiationResponse at an ePrescribing EHR, if the response indicates that prior authorization is required and includes a corresponding question set, answers to these questions are ascertained. In one or more preferred implementations, some or all of such answers may be automatically ascertained based on stored data, while in one or more preferred implementations, a user interface might be presented to a caregiver which prompts the caregiver to answer one or more questions or provide information related to one or more questions.

Figure 7:
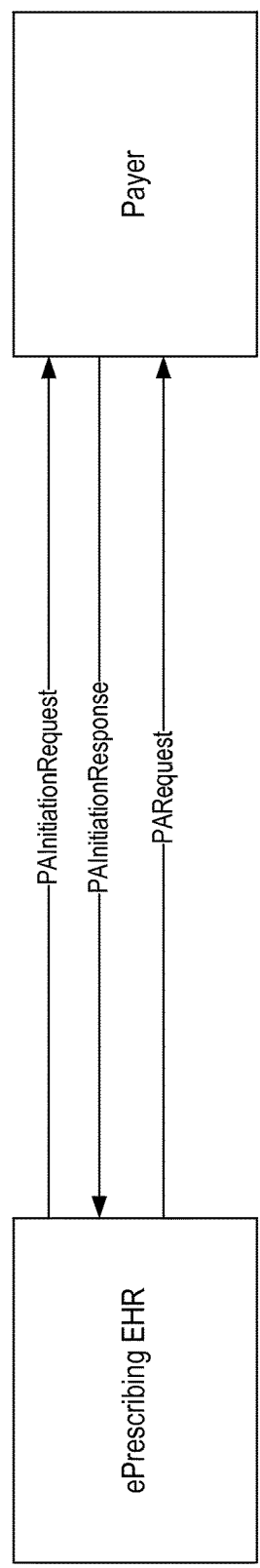
FIG. 7 illustrates communication of a prior authorization request.
Figure 8:
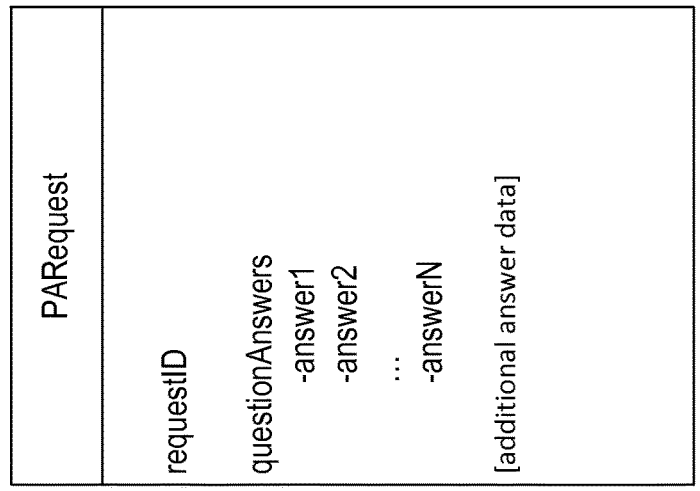
FIG. 8 illustrates from a high level perspective an exemplary prior authorization request.
Figure 9:
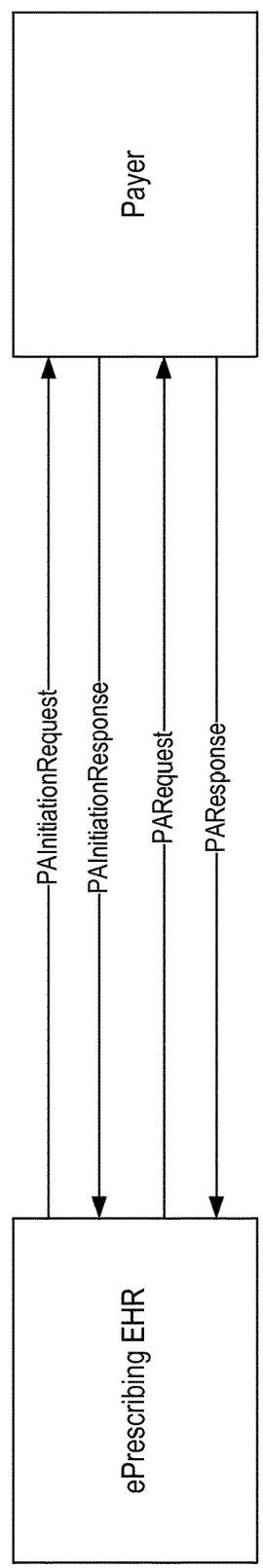
FIG. 9 illustrates communication of a prior authorization response.

Once information related to the received question set is ready, a PARequest is communicated to the payer platform, as illustrated in FIG. 7. The PARequest preferably includes information corresponding to answers to the received question set (although it may or may not be formatted as answers), as illustrated in FIG. 8. The payer platform receives the PARequest containing the information corresponding to answers to the received question set, and makes a determination as to whether to authorize or deny the prior authorization request. This determination is communicated to the ePrescribing EHR in a PAResponse, as illustrated in FIG. 9. In one or more preferred implementations, if a payer platform determines that it does not have enough information to make an authorization decision, a PAResponse might be returned which indicates additional information that is needed to make a determination (for example, this information might be indicated via communication of a question set). In such event, the ePrescribing EHR can obtain the needed information, and send another PARequest to the payer platform.

Figure 10:
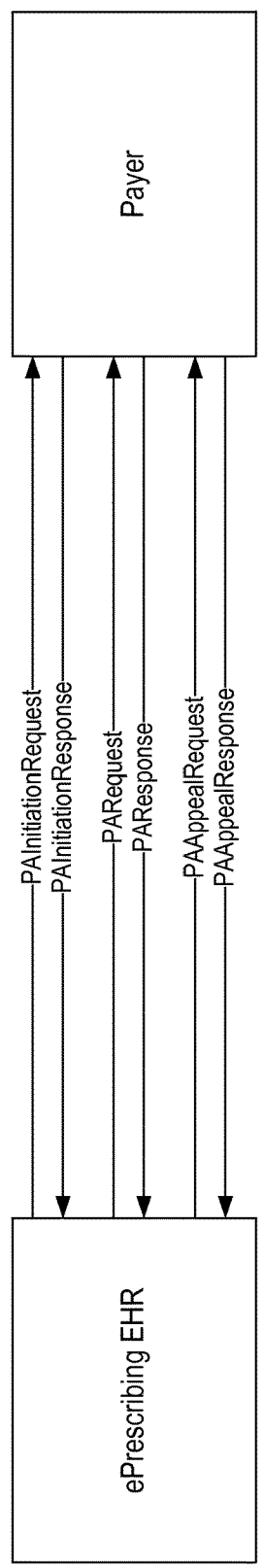
FIG. 10 illustrates communication of a prior authorization appeal request, and a prior authorization appeal response.

In one or more preferred implementations, following receipt of a PAResponse including a determination as to whether a treatment or medication is authorized, a caregiver can choose, via the ePrescribing EHR (or automatically in at least some implementations), to appeal the determination by communicating a PAAppealRequest to the payer platform. An appeal determination will be made by the payer, and communicated to the ePrescribing EHR via a PAAppealResponse, as illustrated in FIG. 10.

Figure 11:
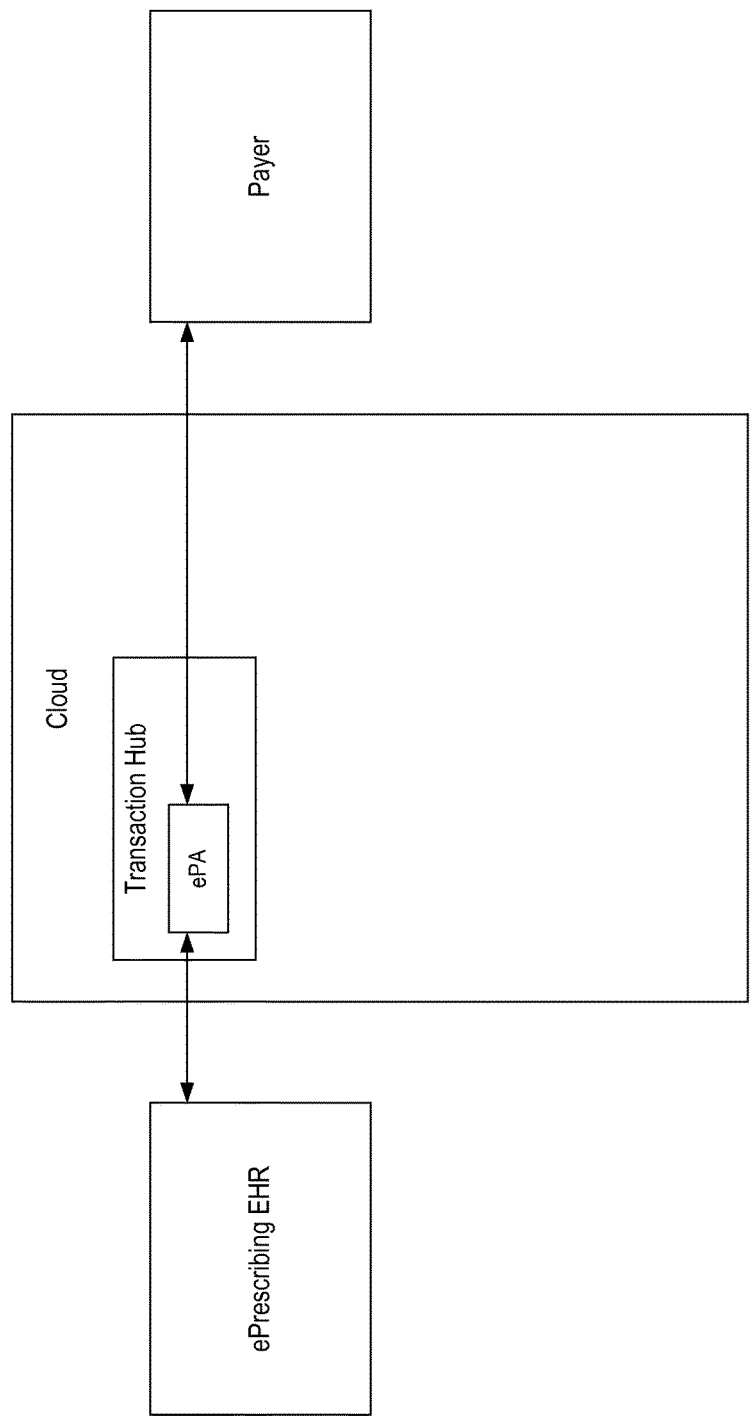
FIG. 11 illustrates a cloud software platform in accordance with one or more preferred implementations.

In one or more preferred implementations, a platform, such as a cloud platform, facilitates communications between an ePrescribing electronic health records (EHR) application associated with a care giver, and a platform associated with a payer. FIG. 11 illustrates such a cloud software platform. As illustrated in FIG. 11, an ePA module of a transaction hub of a cloud platform facilitates communication between an ePrescribing EHR application and a payer platform.

In one or more preferred implementations, accelerator software, which may be, for example running at the cloud platform, is configured to handle some or all ePA messaging for an EHR application. In one or more preferred implementations, such accelerator software is configured to receive a PAInitiationRequest from an EHR, and subsequently facilitate messaging by the EHR by generating messages therefore. For example, in a preferred implementation, an EHR, after sending a PAInitiationRequest to the accelerator software, only has to make a web call to the accelerator software and will receive in return the next message, structured, to the EHR.

In one or more preferred implementations, the accelerator software is configured to provide code (such as JavaScript) to an EHR for generating a user interface for use in connection with a prior authorization request. For example, in one or more preferred implementations, the accelerator software includes question set helper functionality such that, when a question set is returned from a payer, the accelerator software preferably parses the question set, determines what is needed to construct a response, generates tree logic to flow through to arrive at the needed information, and communicates with the EHR to obtain this information. The accelerator software additionally may generate code (e.g. JavaScript) for one or more user interfaces which prompt a user of the EHR application to provide the necessary information. This code is then communicated to the EHR application, which utilizes it to display the corresponding user interface to a user. Information based on user input into such user interfaces can then be provided to the accelerator software, which can utilize it to generate a PARequest including the information requested via a previously received question set.

In one or more preferred implementations, rather than just a PAInitiationRequest being generated by an EHR application, an ePrescribing EHR handles more or all ePA transactions. Alternatively, a cloud platform may handle more or all ePA transactions. In one or more preferred implementations under either or both scenarios, a copy or record of ePA transactions, and/or information communicated therein, is communicated between the EHR ePrescribing application and the cloud platform, e.g. for storage at the cloud platform.

For example, in one or more preferred implementations, an ePrescribing EHR handles all ePA transactions, but communicates a copy of all ePA transactions to the cloud platform. In one or more preferred implementations, the cloud platform is configured to assist the ePrescribing EHR by generating some or all ePA messages for use by the ePrescribing EHR, while in other preferred implementations, all messages are generated by the ePrescribing EHR.

In one or more preferred implementations, all communications with a payer platform are generated and handled by a cloud platform, with parsed, structured messages being sent to an EHR application. For example, a cloud platform might construct messages for a payer platform, communicate the messages to the payer platform, and deconstruct the response into an appropriate schema, for communication to an EHR application.

In one or more preferred implementations, a record or copy of ePA transactions are stored at an ePA message store of the cloud platform. This might include ePA transactions that pass through the cloud platform, are generated at the cloud platform, or for which a copy or data related thereto is communicated to the platform.

Figure 12:
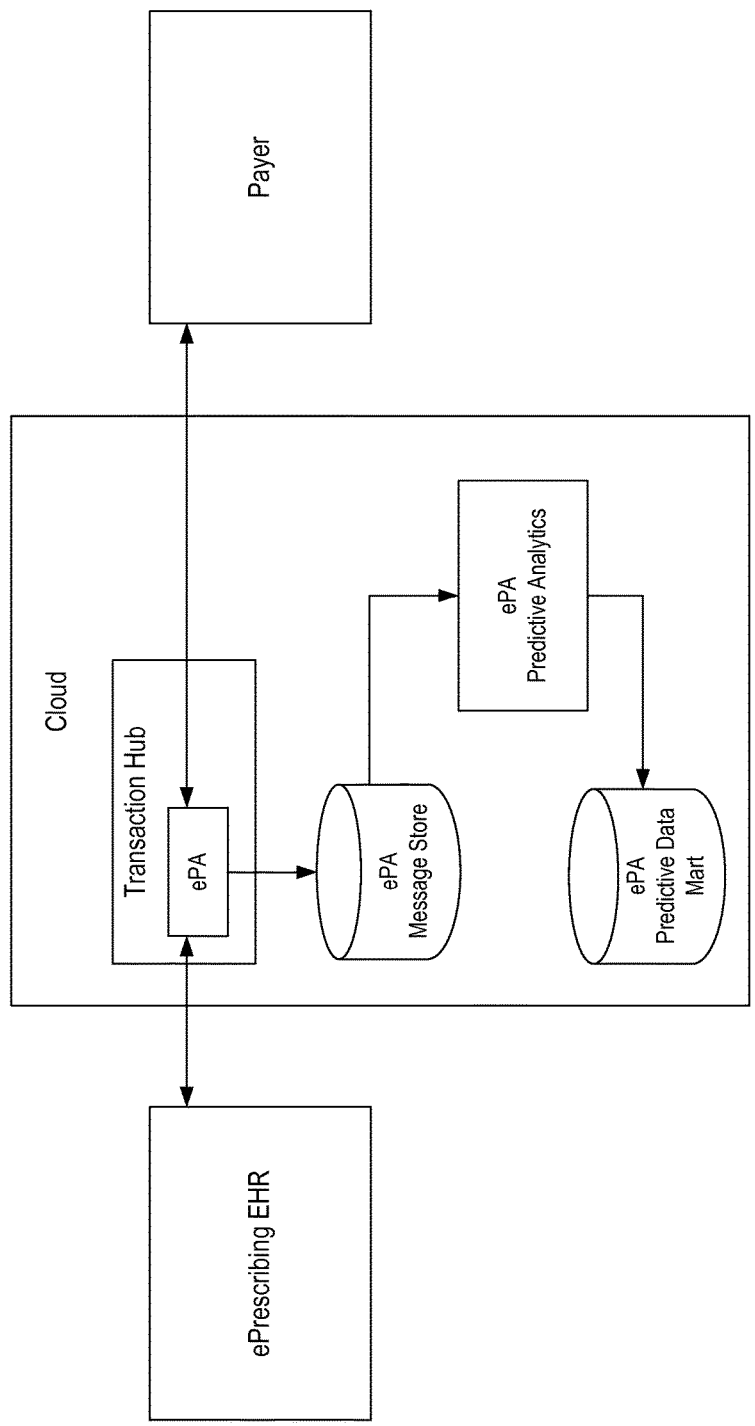
FIG. 12 illustrates exemplary components of a cloud platform configured for analytics processing and storage of prior authorization transaction information.

These transactions are preferably subjected to analytics processing whereby patients, plans, conditions, question sets, appeals, and authorization history are aggregated for storage in an ePA predictive data mart (ePDM), as illustrated in FIG. 12. For example, such analytics processing might collate plans, patients, conditions, medications, and authorizations. In one or more preferred implementations, this ePDM is made available to other ePA consumers, such as subscribers of the cloud platform or other third parties.

Figure 13:
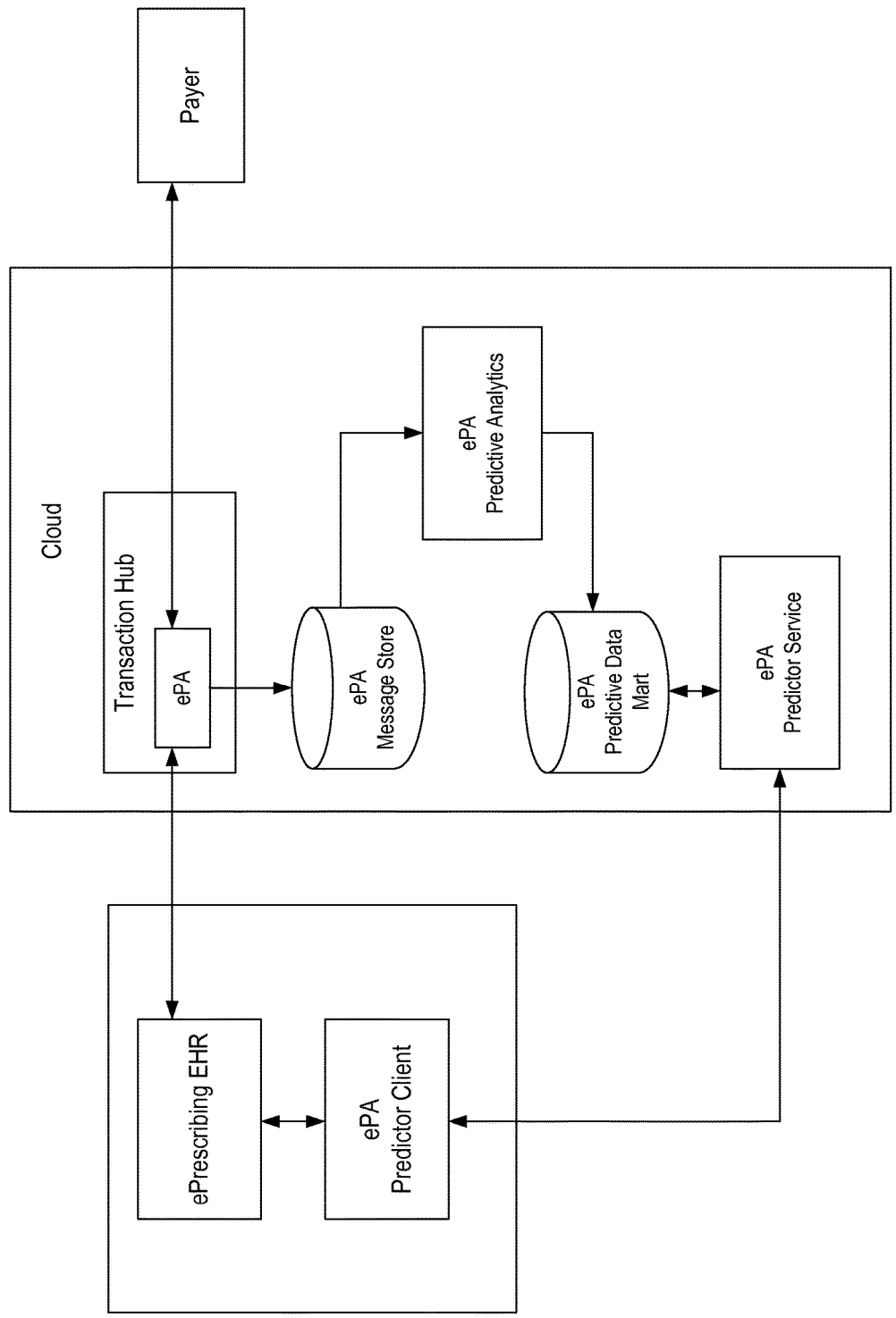
FIGS. 13-14 illustrate the inclusion of a predictor service in a cloud platform in accordance with one or more preferred implementations.

In one or more preferred implementations, data in this ePDM is utilized to make predictions and estimates regarding the likelihood of approval of a particular medication or treatment for a particular condition by a particular payer. In one or more preferred implementations, a cloud platform includes a predictor service configured to provide such predictions. FIG. 13 illustrates a cloud platform which includes such a predictor service.

For example, if the ePDM contains transaction information on one hundred prior authorization requests to Acme Insurance Company for Adderall for treatment of Attention Deficit Hyperactivity Disorder (ADHD), sixty four of which were approved, then the predictor service might estimate the likelihood that Acme Insurance Company will grant a prior approval request for Adderall for the treatment of ADHD to be sixty four percent. In one or more preferred implementations, the predictor service utilizes more complicated predictive methodologies, and may consider, for example, age, gender, insurance plan type, or other biographical data of a particular patient.

Figure 14:
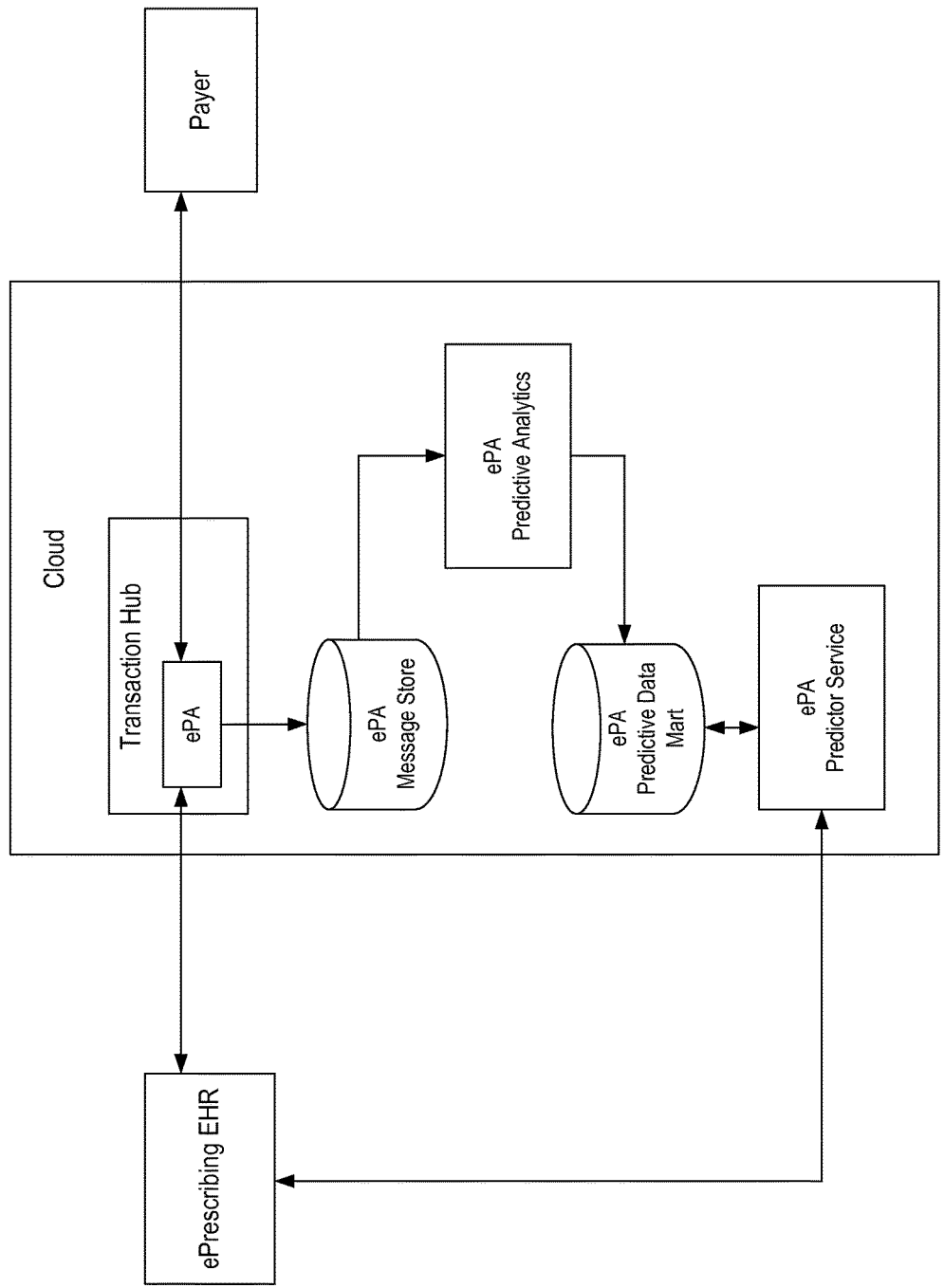

In one or more preferred implementations, a local predictor client interfaces with an ePrescribing EHR and communicates with the predictor service of the cloud platform and receives such estimates, as illustrated in FIG. 13. In at least some preferred implementations, however, such functionality is provided as part of an ePrescribing EHR and the ePrescribing EHR communicates with the predictor service, as illustrated in FIG. 14.

In a preferred methodology, when a care giver selects a medication for a patient (e.g. via a user interface of an ePrescribing EHR, the predictor client communicates information, such as patient, plan, condition, and medication information, to the predictor service, which utilizes data in the predictive data mart to generate an authorization probability. In one or more preferred implementations, recommended alternatives may be determined as well. This may include, in one or more preferred implementations, based on the probability of approval of other alternative medications or treatments, recommending one or more alternative medications or treatments most likely to be authorized for the same condition. This information is preferably then returned to the ePrescribing EHR, for presentation via a user interface of the ePrescribing EHR, as illustrated in FIG. 15. In one or more preferred implementations, if alternative medications are indicated, a user interface will present a similar statement to those illustrated in FIG. 15 for each recommended medication, in descending order of probability.

A workflow model has been described hereinabove where a PAInitializationRequest is sent to a payer platform, which returns a PAInitializationResponse including a question set. This can be characterized as a solicited model, e.g. an ePrescribing EHR solicits a question set for use in preparing a PARequest. In one or more preferred implementations, however, one or more systems endeavor to maintain an understanding of a payer's prior authorization requirements, so that the required information can be included in a first prior authorization transaction (e.g. PARequest) communicated to the payer. This can be characterized as an unsolicited model, e.g. an ePrescribing EHR communicates a PARequest to a payer without first soliciting a question set.

Figure 16:
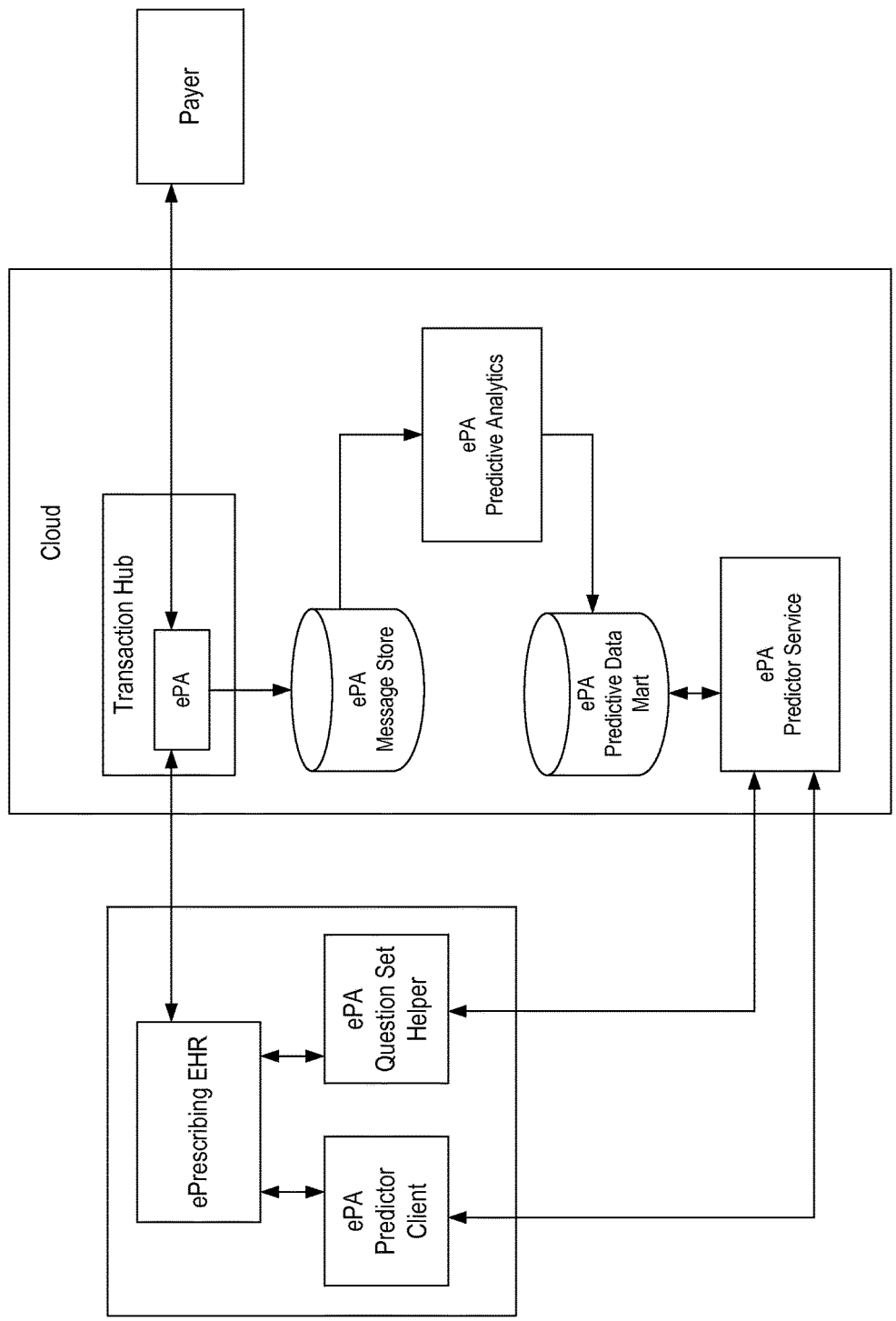
FIGS. 16-18 illustrate various exemplary implementation scenarios for question set builder functionality.
Figure 17:
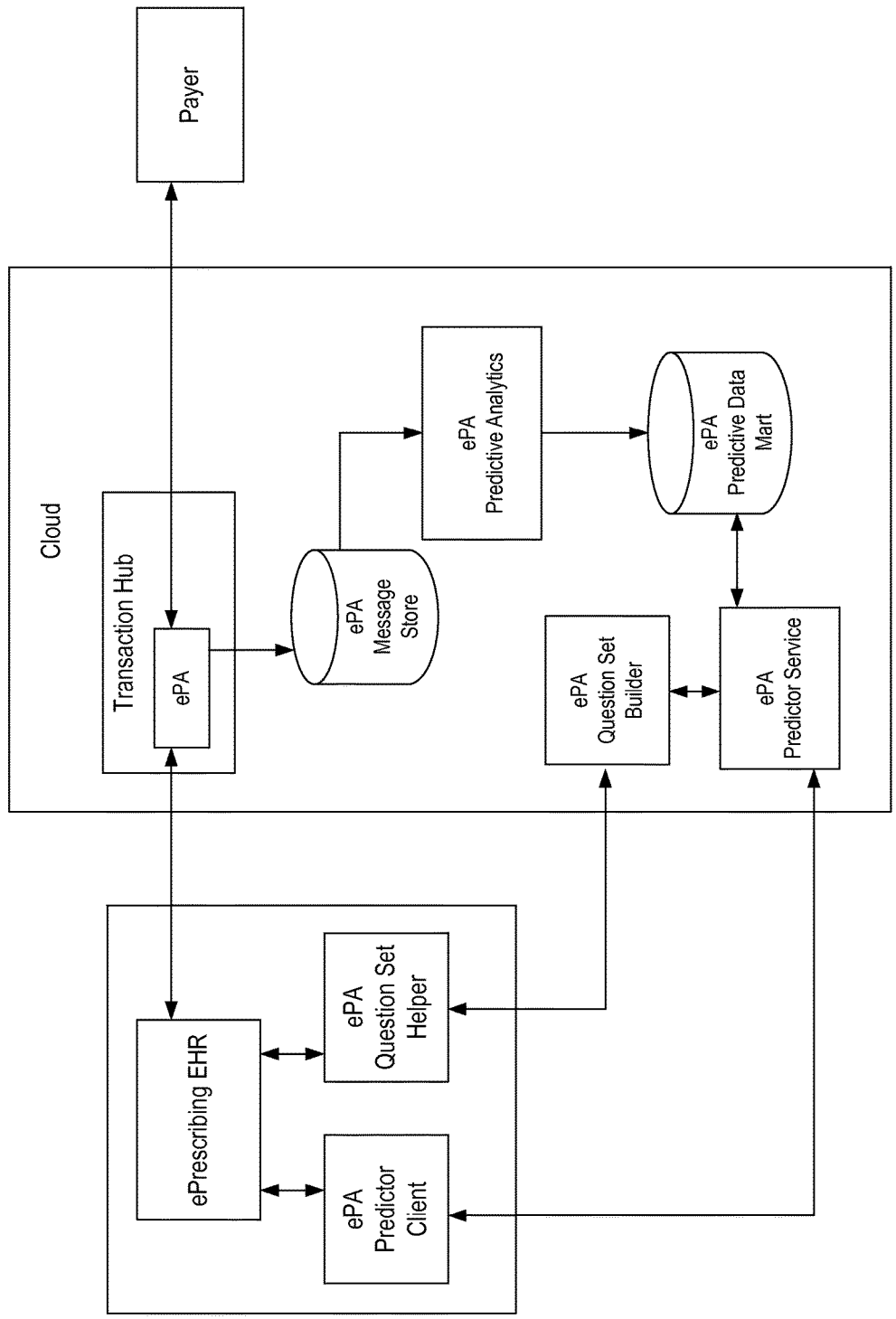
Figure 18:
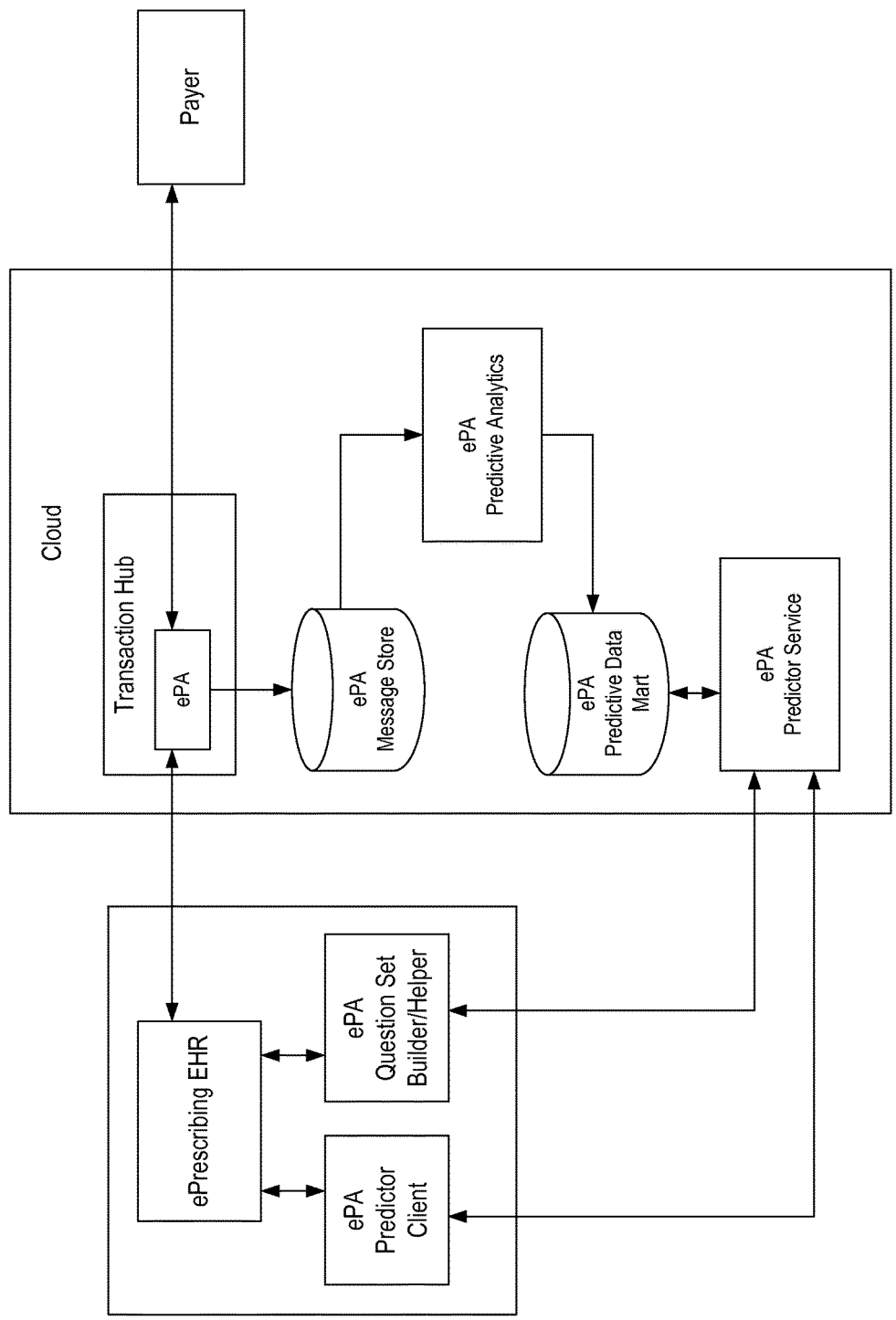

In one or more preferred implementations, a predictive data mart containing stored ePA transactions is utilized to determine the information that will most likely be needed for a prior authorization determination by a particular payer for a particular treatment for a particular condition. In one more preferred implementations, a predictor service queries the predictive data mart to ascertain what information will likely be needed, e.g. queries for a most probable question set for a particular plan (or patient), patient condition, and medication. In one or more preferred implementations, the predictor service may consider, for example, age, gender, insurance plan type, or other biographical data of a particular patient. In one or more preferred implementations, question set builder functionality determines or generates a most probable question set (representing the question set including information that will most likely be needed for a payer to make an authorization decision for a particular medication or treatment for a particular condition). In one or more preferred implementations, question set builder functionality is part of a predictor service, as illustrated in FIG. 16, or part of its own module or service at the cloud platform, as illustrated in FIG. 17. Alternatively, in one or more preferred implementations, question set builder functionality is performed locally at a question set module, as illustrated in FIG. 18.

In one or more preferred implementations, a system includes a question set helper which is configured to facilitate processing of received question sets.

In one or more preferred implementations, a question set helper parses a received question set, determines what is needed to construct a response, generates tree logic to flow through to arrive at the needed information, and communicates with an ePrescribing EHR to obtain this information. The question set helper additionally may generate a user interface (or code therefor) which prompts a user of an EHR application to provide any necessary information.

Question set helper functionality preferably includes identifying and managing the sequencing of questions based on an order indicated in the question set and on answers to questions provided by a care giver, storing and maintaining answers, allowing a user to clear previously answered questions, allowing a user to restart at the beginning of a question set, and allowing a user to attach a file to a question set. In one or more preferred implementations, a question set helper optionally interfaces with an EHR to automatically discover some information. Preferably, information based on user input into such user interfaces is utilized to generate a PARequest.

In one or more preferred implementations, if a payer receiving a generated PARequest determines that additional information is needed to make an authorization determination (e.g. because a predicted question set did not include all of the information needed to make an authorization determination), the payer preferably returns a PAResponse including a question set corresponding to information needed to make the authorization determination. This question set may only correspond to additional information, or it may correspond to all information needed to make the determination.

In one or more preferred implementations, a question set helper is configured to function with both a predicted question set and a question set received from a payer (e.g. in a PAInitiationResponse or PAResponse).

It will be appreciated that the accelerator software described hereinabove can include question set helper functionality similar to that provided by a question set builder.

Figure 19:
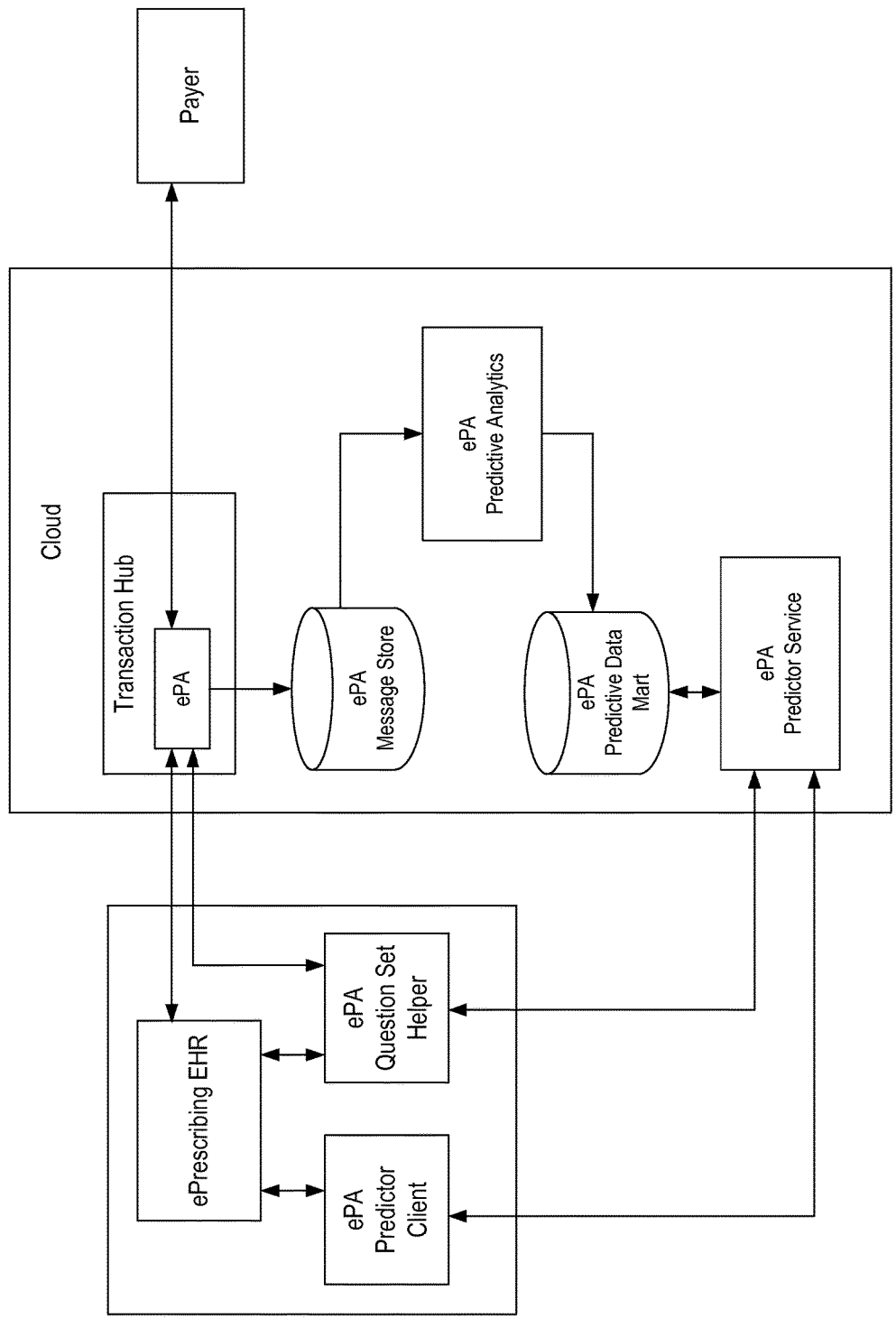
FIGS. 19-21 illustrate various exemplary implementation scenarios for question set helper functionality.
Figure 20:
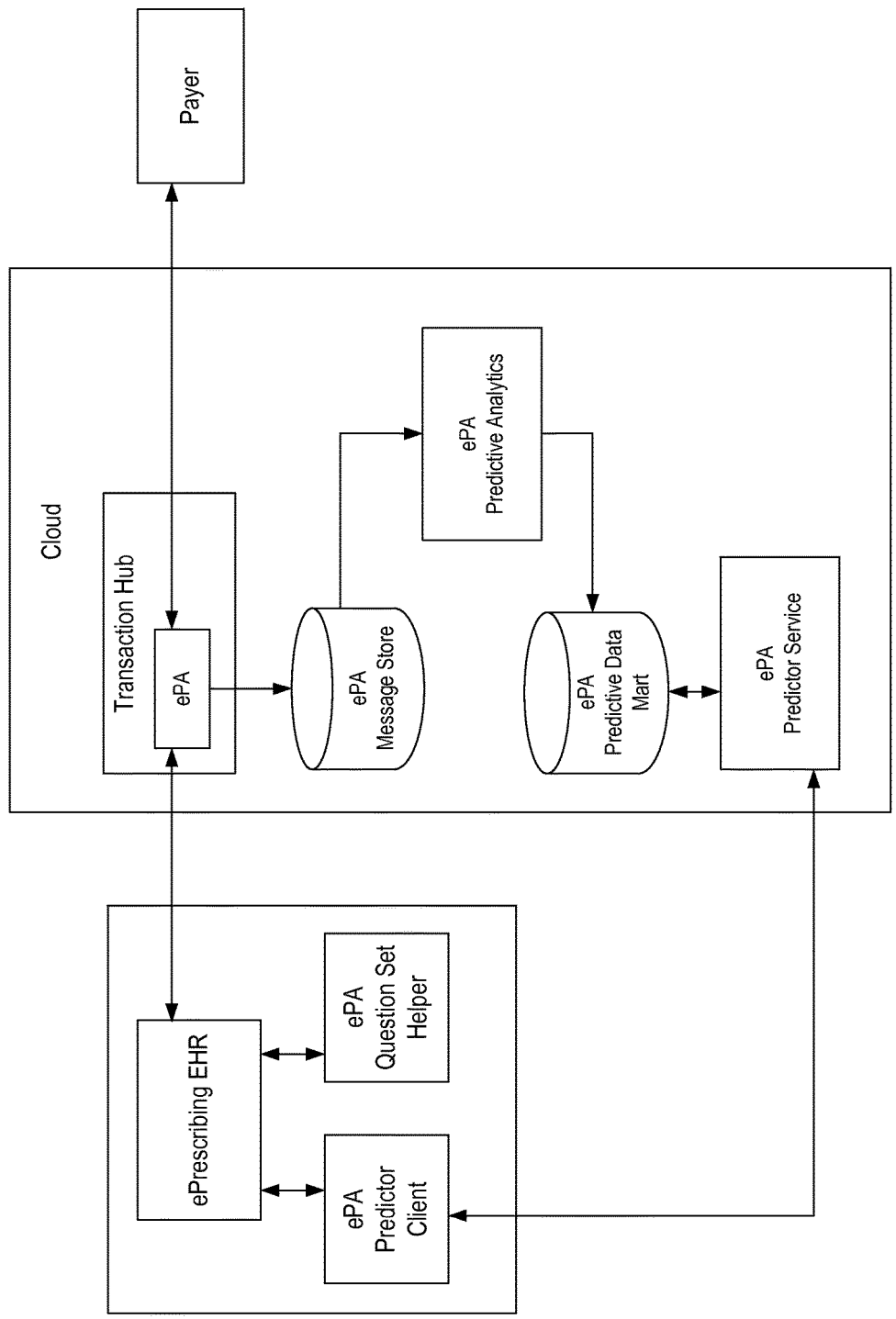
Figure 21:
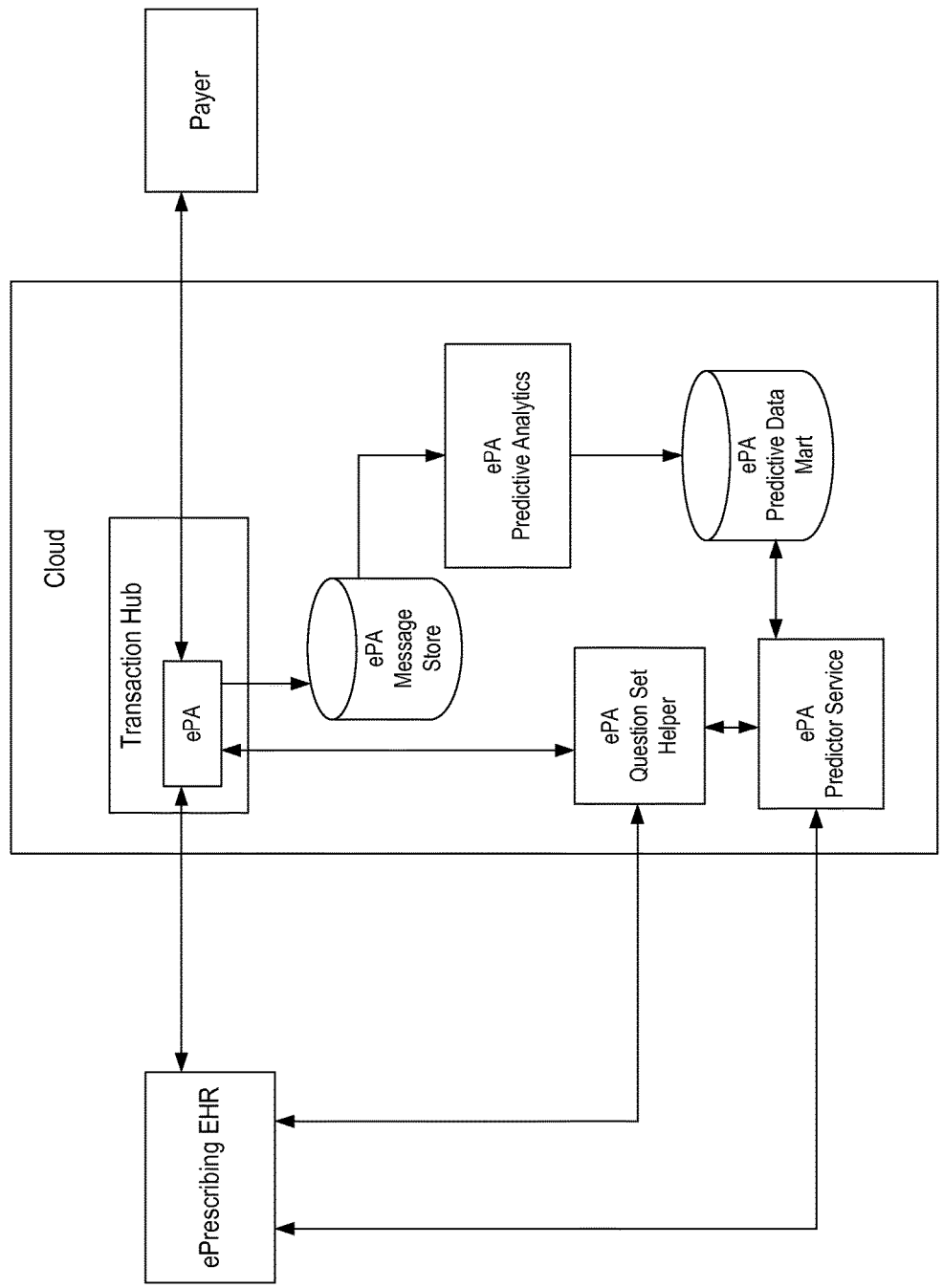

More generally, question set helper functionality (e.g. question set helper software or a question set helper module), can be provided locally, or at a cloud platform, and can interface with various components in various workflows. For example, in one or more preferred implementations, a local question set helper is configured to receive a predicted question set from a predictor service and interface with an ePrescribing EHR, as illustrated in FIG. 16. In one or more preferred implementations, a question set helper is configured to similarly receive a question set originating from a payer, as illustrated in FIG. 19. In one or more preferred implementations, a question set helper is configured for use with question sets received by an ePrescribing EHR, as illustrated in FIG. 20. In one or more preferred implementations, a question set helper is located at a cloud platform, as illustrated in FIG. 21.

Figure 22:
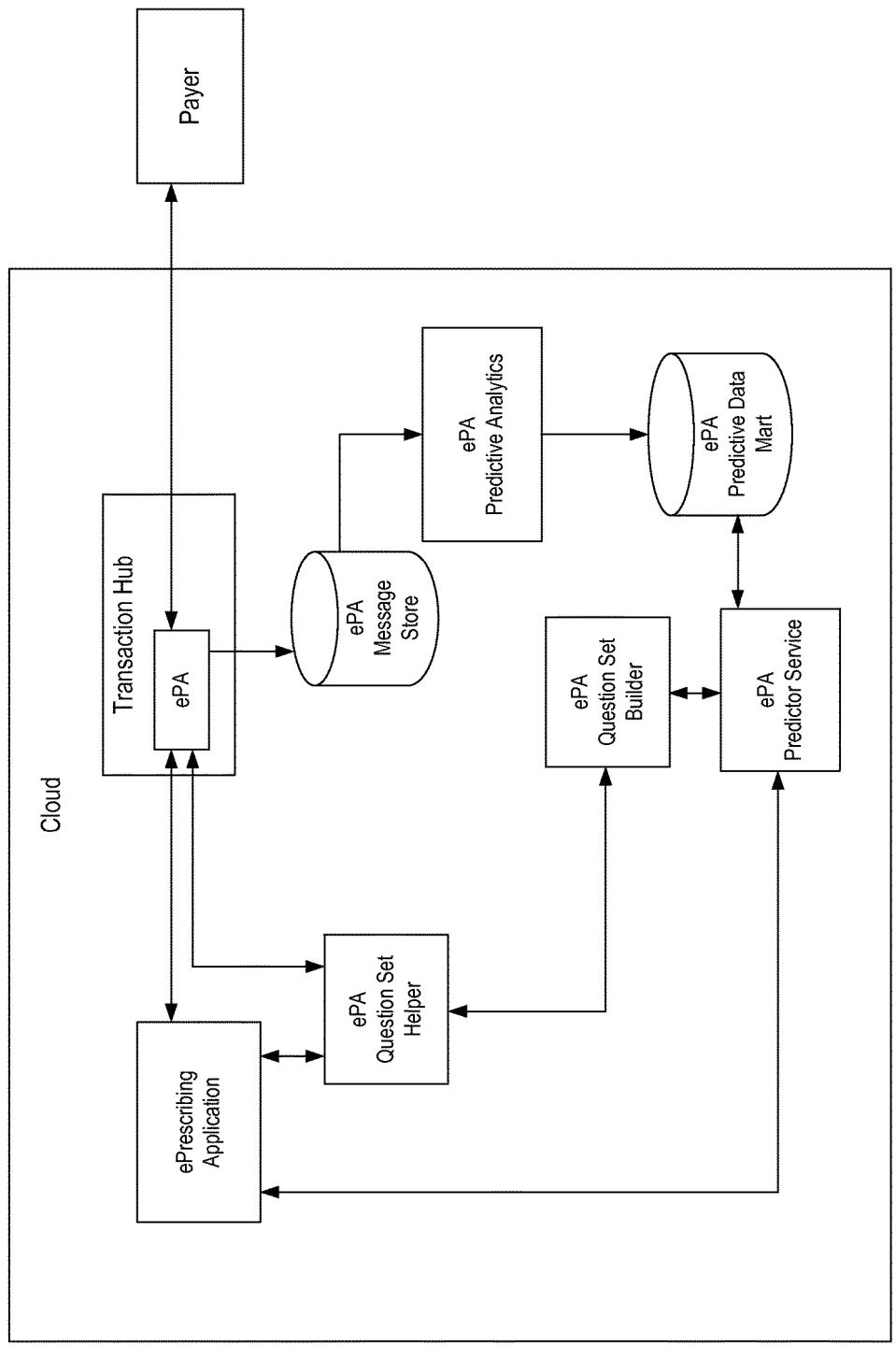
FIG. 22 illustrates an implementation including an ePrescribing application at a cloud platform.

Although thus far described in the context of a local ePrescribing EHR, in one or more preferred implementations systems, methodologies, and functionality described herein is utilized with other applications, both installed locally at one or more computing devices, and loaded at a cloud. For example, FIG. 22 illustrates an implementation including an ePrescribing application at a cloud platform.

In accordance with one or more preferred implementations, pharmacy benefits managers (PBMs), which are third party administrators of prescription drug programs, may wish to provide question sets matched to medications and insurance plans. However, some PBMs (such as, for example, second and third tier PBMs) may not have the technical capability or tooling able to generate an NCPDP Question Set.

Figure 23:
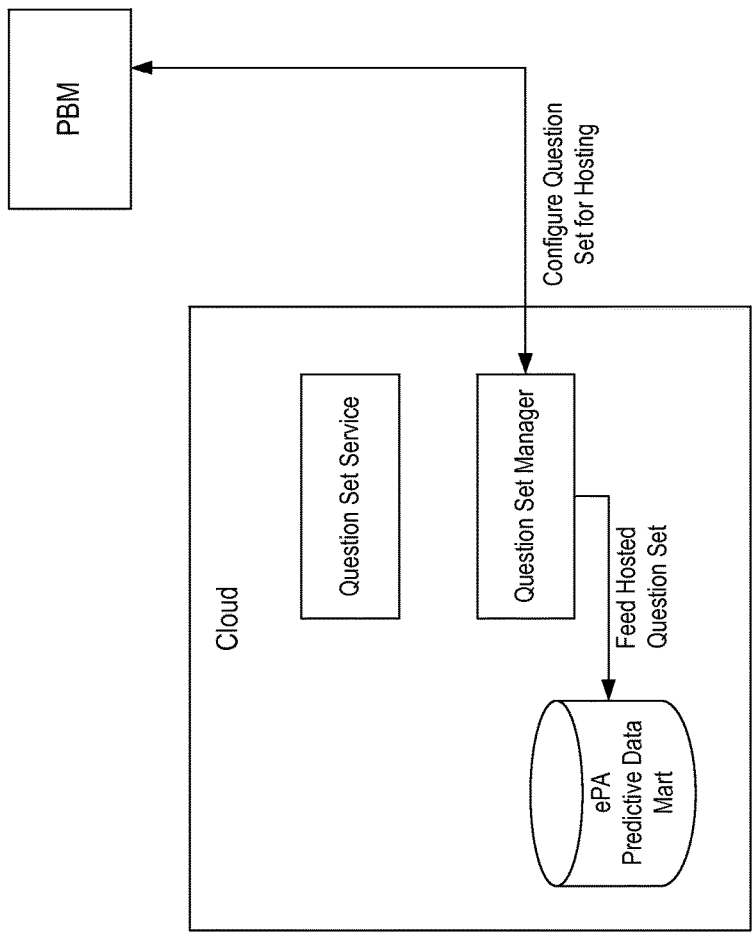
FIG. 23 illustrates a question set manager.

In one or more preferred implementations, a question set manager is configured to allow a user to create header information, specific questions, and the associated tree logic to create an approved question set, and host that question set in a cloud platform, as illustrated in FIG. 23. In one or more preferred implementations, such a hosted question set is also fed to an ePA Predictive Data Mart, as illustrated.

Figure 24:
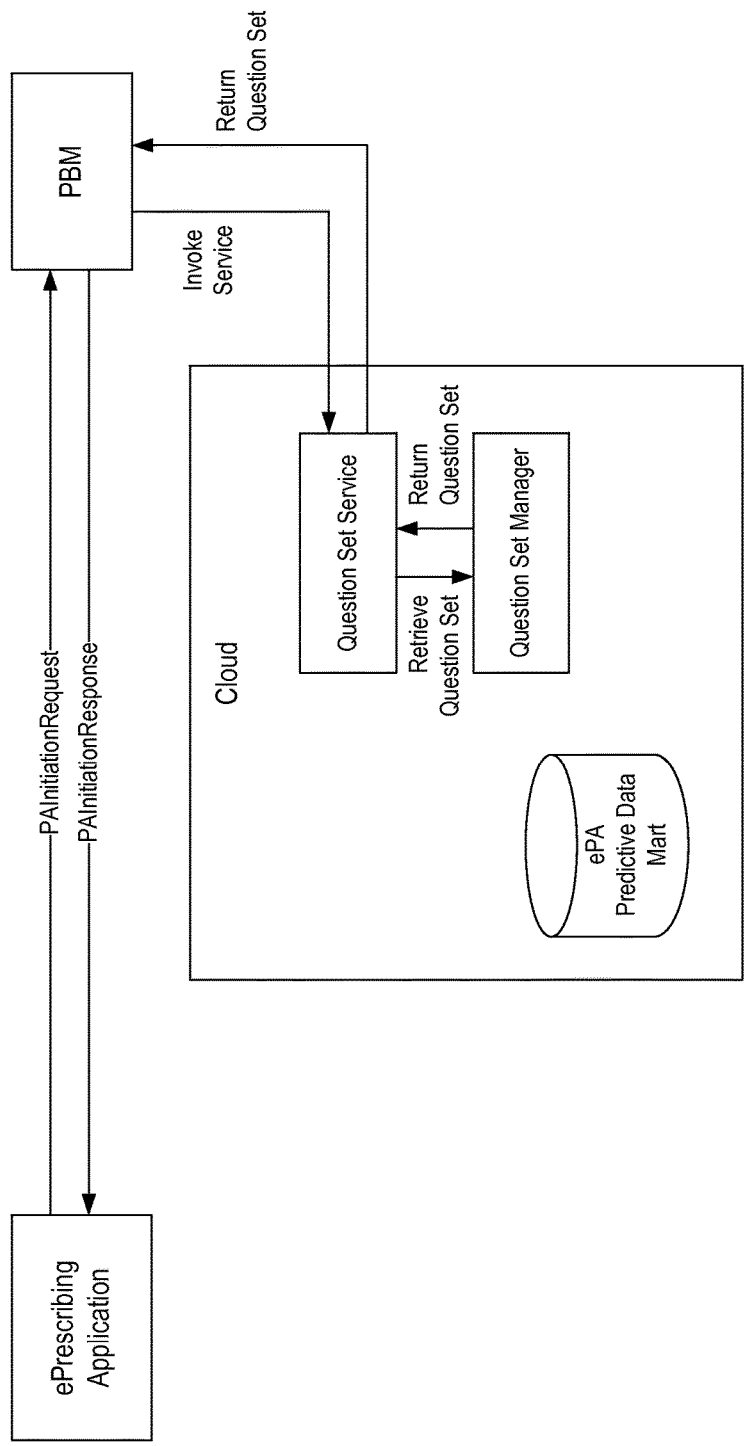
FIG. 24 illustrates use of a question set service to retrieve a question set.

In one or more preferred implementations, thereafter, when a PAInitiationRequest is received from an ePrescribing application, the PBM invokes an ePA question set service to retrieve and return a hosted question set, as illustrated in FIG. 24. This question set can then be provided in a PAInitiationResponse communicated back to the ePrescribing application.

Figure 25:
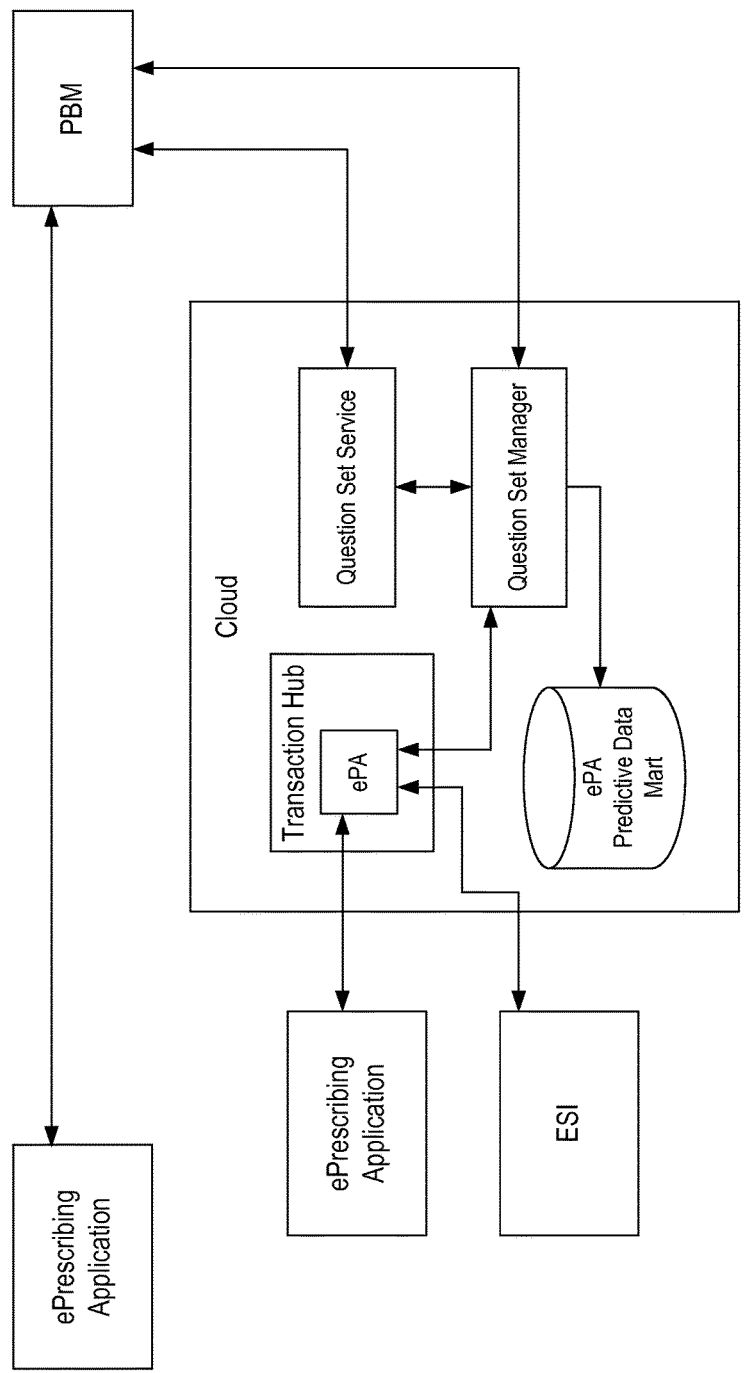
FIG. 25 illustrates a preferred implementation in which a transaction hub of a cloud platform is configured to interface with a question set manager of a cloud platform.

Such a question set manager can be utilized in combination with other software and components described herein as well, such as software of a cloud platform. For example, in one or more preferred implementations in which a cloud platform is configured to facilitate ePA transactions for ePrescribing applications, a transaction hub is configured to interface with a question set manager to retrieve question sets, as illustrated in FIG. 25.

Figure 26:
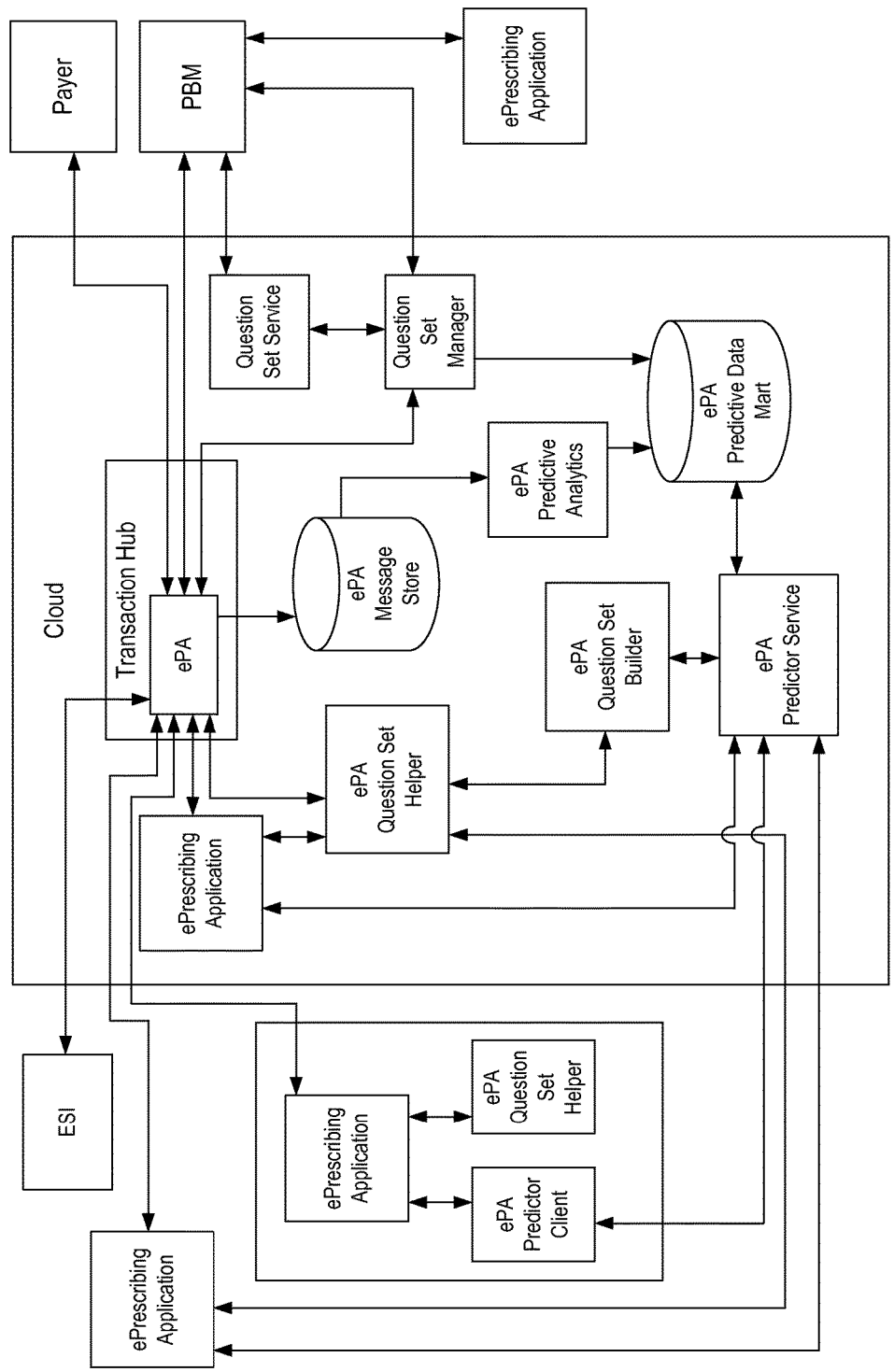
FIG. 26 illustrates from a high level perspective exemplary communication between components in an exemplary system which includes a number of exemplary ePrescribing applications.

FIG. 26 illustrates from a high level perspective exemplary communication between components in an exemplary system which includes a number of exemplary ePrescribing applications, such as a cloud ePrescribing application and an off the base (OTB) ePrescribing application, configured to engage in ePA transactions in various ways, such as, for example, directly or indirectly through a cloud platform. The system further includes an exemplary PBM and payer.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for facilitating communication of an electronic authorization request for medication by utilizing historical information to predict what information will be needed for evaluating an authorization request, the method comprising:
   (a) receiving, at an electronic health records application, first user input from a care giver input via one or more input devices associated with an electronic device, the first user input corresponding to an indication of a proposed medication for treatment of a condition of a patient;
   (b) communicating, from the electronic health records application to a predictor service at a cloud platform, data corresponding to an identification of a payer associated with the patient, an identification of the condition, and an identification of the proposed medication;
   (c) accessing, by the predictor service at the cloud platform from a predictive data mart at the cloud platform which contains historical data on prior authorization transactions, historical transaction data corresponding to information indicated to be necessary for authorization decisions by the payer for use of the proposed medication for treatment of the condition;
   (d) predicting, by the predictor service based on the accessed historical transaction data, what information will be necessary for an authorization decision by the payer for use of the proposed medication for treatment of the condition, and generating, based on the information predicted to be necessary for an authorization decision, a predicted question set;

(e) communicating, by the cloud platform, data associated with the predicted question set to the electronic health records application;

(f) displaying, via a display screen associated with the electronic device, a question to the care giver based on the data associated with the predicted question set communicated to the electronic health records application;

(g) receiving, from the caregiver via one or more input devices associated with the electronic device, second user input corresponding to an answer to the displayed question;

(j) communicating, from the electronic health records application to the cloud platform, data associated with the answer to the displayed question;

(k) communicating, from the cloud platform to a platform associated with the payer, an authorization request including data associated with the answer to the displayed question;

(l) receiving, at the cloud platform from the platform associated with the payer, an authorization response including an indication of whether authorization of the medication for treatment of the condition for the patient is granted, and communicating data corresponding to such indication to the electronic health records application.

2. The method of claim 1, wherein the electronic device comprises a tablet.

3. The method of claim 1, wherein the electronic device comprises a laptop.

4. The method of claim 1, wherein the electronic device comprises a phone.

5. The method of claim 1, wherein receiving first user input comprises receiving first user input input via a touchscreen.

6. The method of claim 1, wherein receiving first user input comprises receiving first user input input via a mouse.

7. The method of claim 1, wherein receiving first user input comprises receiving first user input input via a keyboard.

8. The method of claim 1, wherein the identification of the condition of the patient comprises a medical code.

9. The method of claim 1, wherein the identification of the medication comprises an identification number associated with a medication.

10. The method of claim 1, wherein the identification of the payer comprises a payer code.

11. A method for facilitating communication of an electronic authorization request for medication by utilizing historical information to predict what information will be needed for evaluating an authorization request, the method comprising:

(a) receiving, at an electronic health records application, first user input from a care giver input via one or more input devices associated with an electronic device, the first user input corresponding to an indication of a proposed medication for treatment of a condition of a patient;

(b) communicating, from the electronic health records application to a predictor service at a cloud platform, data corresponding to an identification of a payer associated with the patient, an identification of the condition, and an identification of the proposed medication;

(c) accessing, by the predictor service at the cloud platform from a predictive data mart at the cloud platform which contains historical data on prior authorization transactions, historical transaction data corresponding to question sets for authorization decisions by the payer for use of the proposed medication for treatment of the condition;

(d) predicting, by the predictor service based on the accessed historical transaction data, what information will be necessary for an authorization decision by the payer for use of the proposed medication for treatment of the condition, and generating, based on the information predicted to be necessary for an authorization decision, a predicted question set;

(e) communicating, by the cloud platform, data associated with the most probable question set to the electronic health records application;

(f) displaying, via a display screen associated with the electronic device, a question to the care giver based on the data associated with the most probable question set communicated to the electronic health records application;

(g) receiving, from the caregiver via one or more input devices associated with the electronic device, second user input corresponding to an answer to the displayed question;

(j) communicating, from the electronic health records application to the cloud platform, data associated with the answer to the displayed question;

(k) communicating, from the cloud platform to a platform associated with the payer, an authorization request including data associated with the answer to the displayed question;

(l) receiving, at the cloud platform from the platform associated with the payer, an authorization response including an indication of whether authorization of the medication for treatment of the condition for the patient is granted, and communicating data corresponding to such indication to the electronic health records application.

12. The method of claim 11, wherein the electronic device comprises a tablet.

13. The method of claim 11, wherein the electronic device comprises a laptop.

14. The method of claim 11, wherein the electronic device comprises a phone.

15. The method of claim 11, wherein receiving first user input comprises receiving first user input input via a touchscreen.

16. The method of claim 11, wherein receiving first user input comprises receiving first user input input via a mouse.

17. The method of claim 11, wherein receiving first user input comprises receiving first user input input via a keyboard.

18. The method of claim 11, wherein the identification of the condition of the patient comprises a medical code.

19. The method of claim 11, wherein the identification of the medication comprises an identification number associated with a medication.

20. A method for facilitating communication of an electronic authorization request for medication by utilizing historical information to predict what information will be needed for evaluating an authorization request, the method comprising:

(a) receiving, at an electronic health records application, first user input from a care giver input via one or more input devices associated with an electronic device, the first user input corresponding to an indication of a proposed medication for treatment of a condition of a patient;

(b) communicating, from the electronic health records application to a cloud platform, data corresponding to an identification of a payer associated with the patient, an identification of the condition, and an identification of the proposed medication;

(c) accessing, by the cloud platform from a predictive data mart at the cloud platform which contains historical data on prior authorization transactions, historical transaction data corresponding to information indicated to be necessary for authorization decisions by the payer for use of the proposed medication for treatment of the condition;

(d) predicting, based on the accessed historical transaction data, what information will be needed for an authorization decision by the payer for use of the proposed medication for treatment of the condition, and generating, based on the information predicted to be needed for an authorization decision, a predicted question set;

(e) displaying, via a display screen associated with the electronic device, a question to the care giver based on the determined most probable question;

(f) receiving, from the caregiver via one or more input devices associated with the electronic device, second user input corresponding to an answer to the displayed question;

(g) communicating, from the cloud platform to a platform associated with the payer, an authorization request including data associated with the answer to the displayed question; and (h) receiving, at the cloud platform from the platform associated with the payer, an authorization response including an indication of whether authorization of the medication for treatment of the condition for the patient is granted, and communicating data corresponding to such indication to the electronic health records application.

* * * * *